US006528625B1

(12) United States Patent
Wu et al.

(10) Patent No.: US 6,528,625 B1
(45) Date of Patent: Mar. 4, 2003

(54) ANTI-CCR5 ANTIBODIES AND KITS COMPRISING SAME

(75) Inventors: Lijun Wu, Lexington, MA (US); Charles R. Mackay, Watertown, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 08/893,911

(22) Filed: Jul. 11, 1997

Related U.S. Application Data

(63) Continuation-in-part of application No. 08/739,507, filed on Oct. 28, 1996, now abandoned.

(51) Int. Cl.[7] .......................... C07K 16/28; C12N 5/12; A61K 39/395
(52) U.S. Cl. ............... 530/388.22; 530/387.1; 530/387.3; 530/388.1; 530/388.2; 530/388.7; 530/388.73; 530/388.75; 530/389.1; 530/389.2; 530/389.6; 530/866; 435/326; 435/328; 435/332; 435/334; 435/346; 435/810; 435/70.2; 435/70.21; 424/130.1; 424/133.1; 424/136.1; 424/141.1; 424/143.1; 424/152.1; 424/153.1; 424/154.1
(58) Field of Search .................. 530/388.22, 369.2, 530/387.1, 866, 387.3, 388.1, 388.2, 388.7, 388.73, 388.75, 389.1, 389.6; 435/76.2, 76.21, 810, 326, 328, 332, 334, 346; 424/130.1, 133.1, 136.1, 141.1, 143.1, 152.1, 153.1, 154.1, 172.1, 173.1

(56) References Cited

U.S. PATENT DOCUMENTS

| | | | |
|---|---|---|---|
| 5,440,021 A | | 8/1995 | Chuntharapai et al. |
| 5,543,503 A | | 8/1996 | Chuntharapai et al. |
| 5,939,320 A | * | 8/1999 | Littman et al. |
| 5,994,515 A | | 11/1999 | Hoxie |
| 6,025,154 A | | 2/2000 | Li et al. |
| 6,057,102 A | | 5/2000 | Landau et al. |

FOREIGN PATENT DOCUMENTS

| | | |
|---|---|---|
| DE | 43 32 256 C1 | 3/1995 |
| WO | WO 95/08576 | 3/1995 |
| WO | WO 96/39437 | 12/1996 |
| WO | WO 97/22698 | 6/1997 |
| WO | WO 97/26009 | 7/1997 |
| WO | WO 97/32019 | 9/1997 |
| WO | WO 97/41225 | 11/1997 |
| WO | WO 97/44055 | 11/1997 |
| WO | WO 97/45543 | 12/1997 |
| WO | WO 97/47319 | 12/1997 |
| WO | WO 98/00535 | 1/1998 |
| WO | WO 98/05798 | 2/1998 |
| WO | WO 98/18826 | 5/1998 |
| WO | WO 98/44953 | 10/1998 |
| WO | WO 98/54317 | 12/1998 |
| WO | WO 99/15666 | 4/1999 |
| WO | WO 00/53633 | 9/2000 |

OTHER PUBLICATIONS

Zlotnik and Yoshie Immunity 2000;12:121–127.*
Mackay Nature Immunol. 2001;2:95–101.*
Chuntharapai, et al., "Generation of Monoclonal Antibodies to Chemokine Receptors", *Methods in Enzymology* 288: 15–27 (Sep. 1997).
Dean, M., et al., "Genetic Restriction of HIV–1 Infection and Progression to AIDS by a Deletion Allele of the CKR5 Structural Gene", *Science*, 273:1856–1862 (1996).
Liu, R., et al., "Homozygous Defect in HIV–1 Coreceptor Accounts for Resistance of Some Multiply–Exposed Individuals to HIV–1 Infection", *Cell*, 86:367–377 (1996).
Bates, P., "Chemokine Receptors and HIV–1: An Attractive Pair?", *Cell*, 86:1–3 (1996).
Choe, H., et al., "The β–Chemiokine Receptors CCR3 and CCR5 Facilitate Infection by Primary HIV–1 Isolates", *Cell*, 85:1135–1148 (1996).
Samson, M., et al., "Molecular Cloning and Functional Expression of a New Human CC–Chemokine Receptor Gene", *Biochemistry*, 35:3362–3367 (1996).
Raport, C.J., et al., "Molecular Cloning and Functional Characterization of a Novel Human CC Chemokine Receptor (CCR5) for RANTES, MIP–1β, and MIP–1α", *Jour. of Biol. Chem.*, 271(29): 17161–17166 (1996).
Boring, L., et al., "Molecular Cloning and Functional Expression of Murine JE (Monocyte Chemoattractant Protein 1) and Murine Macrophage Inflammatory Protein 1α Receptors", *Jour. of Biol. Chem.*, 271 (13): 7551–7558 (1996).
Weiss, R.A. and Clapham, P.R., "Hot Fusion of HIV", *Nature*, 381:647–648 (1996).
Deng, H., et al., "Identification of a Major Co–Receptor for Primary Isolates of HIV–1", *Nature*, 381:661–666 (1996).
Dragic, T., et al., "HIV–1 Entry Into CD4+ Cells is Mediated by the Chemokine Receptor CC–CKR–5", *Nature*, 381:667–673 (1996).
Hill, C.M. and Littman, D.R., "Natural Resistance to HIV?", *Nature*, 382:668–669 (1996).
Samson, M., et al., "Resistance to HIV–1 Infection in Caucasian Individuals Bearing Mutant Alleles of the CCR–5 Chemokine Receptor Gene", *Nature*, 382:722–725 (1996).

(List continued on next page.)

*Primary Examiner*—Phillip Gambel
*Assistant Examiner*—Jessica H. Roark
(74) *Attorney, Agent, or Firm*—Hamilton, Brook, Smith & Reynolds, P.C.

(57) ABSTRACT

The present invention relates to an antibody or functional portion thereof which binds to a mammalian (e.g., human) chemokine receptor 5 protein (CKR-5 or CCR5) or portion of the receptor. The invention further relates to a method of inhibiting the interaction of a cell bearing mammalian CCR5 with a ligand thereof. Another aspect of the invention relates to a method of inhibiting HIV infection of a cell which expresses a mammalian CCR5 or portion thereof using the antibodies described herein. Also encompassed by the present invention are methods of treating or preventing HIV in a patient.

36 Claims, 17 Drawing Sheets

OTHER PUBLICATIONS

Doranz, B.J., et al., "A Dual–Tropic Primary HIV–1 Isolate That Uses Fusin and the β–Chemokine Receptors CKR–5, CKR–3, and CKR–2b as Fusion Cofactors", *Cell*, 85:1149–1158 (1996).

Feng, Y., et al., "HIV–1 Entry Cofactor: Functional cDNA Cloning of a Seven–Transmembrane, G Protein–Coupled Receptor", *Science*, 272:872–877 (1996).

Cocchi, F., et al., "Identification of RANTES, MIP–1α, and MIP–1β as the Major HIV–Suppressive Factors Produced by CD8+ T Cells", *Science*, 270:1811–1815 (1995).

Alkhatib, G., et al., "CC CKR5: A RANTES, MIP–1α, MIP–1β Receptor as a Fusion Cofactor for Macrophage–Tropic HIV–1", *Science*, 272:1955–1958 (1996).

Förster, R. et al., "A General Method for Screening mAbs Specific for G–protein Coupled Receptors as Exemplified by Using Epitope Tagged BLR1–transfected 293 Cells and Solid–phase Cell ELISA", *Biochem. Biophys. Res. Commun.*, 196(3):1496–1503 (1993).

Raport, C.J., et al., "New Members of Chemokine Receptor Gene Family", *J. Of Leukocyte Biol.*, 59:18–23 (1996).

Combadiere, C., et al., "Cloning and Functional Expression of a Human Eosinophil CC Chemokine Receptor", *The Jour. of Biol. Chem.*, 270 (27):16491–16494 (1995).

Wasniowska, K., et al., "Identification of the Fy6 Epitope Recognized by Two Monoclonal Antibodies in the N–Terminal Extracellular Portion of the Duffy Antigen Receptor for Chemokines", *Molec. Immunol.*, 33(11/12):917–923 (1996).

Combadiere, C., et al., "Cloning and Functional Expression of CC CKR5, A Human Monocyte CC Chemokine Receptor Selective for MIP–1α, MIP–1β, and RANTES", *J. of Leukocyte Biol.*, 60:147–152 (1996).

Ponath, P.D., et al., "Molecular Cloning and Characterization of a Human Eotaxin Receptor Expressed Selectively on Eosinophils", *J. Exp. Med.*, 183:2437–2448 (1996).

Rudikoff, S., et al., "Single Amino Acid Substitution Altering Antigen–binding Specificity," *Proc. Natl. Acad. Sci. USA*, 79:1979–1983 (1982).

Wildner, G., and Thurau, S.R., "Database Screening for Molecular Mimicry", *Immunology Today*, 18(5):252–253 (1997).

Berzofsky, J.A. and Berkower, I.J., "Immunogenicity and Antigen Structure." In *Fundametal Immunology, Second Edition*, W.E. Paul, ed. (NYL Raven Press Ltd.) pp. 169–208 (1989).

Neote, K., et al., "Molecular Cloning, Functional Expression, and Signaling Characteristics of a C–C Chemokine Receptor", *Cell*, 72:415–425 (1993).

Endres, M.J., et al., "CD4–Independent Infection by HIV–2 Is Mediated by Fusin/CXCR4", *Cell*, 87:745–756 (1996).

Su, S., et al., "Preparation of Specific Polyclonal Antibodies to a C–C Chemokine Receptor, CCR1, and Determination of CCR1 Expression on Various Types of Leukocytes", *J. of Leukocyte Bio.*, 60:658–666 (1996).

Wu, Lijun, et al., "Interaction of Chemokine Receptor CCR5 with its Ligands: Multiple Domains for HIV–1 gp120 Binding and a Single Domain for Chemokine Binding", *J. Exp. Med.*, 186(8):1373–1381 (1997).

Wu, Lijun, et al., "CCR5 Levels and Expression Pattern Correlate with Infectability by Macrophage–tropic HIV–1, In Vitro", *J. Exp. Med.*, 1859):1681–1691 (1997).

Bleul, Conrad C., et al., "The HIV Coreceptors CXCR4 and CCR5 are Differentially Expressed and Regulated on Human T Lymphocytes", *Proc. Natl. Acad. Sci.*, 94:1925–1930 (1997).

Doranz, Benjamin J., et al., "Two Distinct CCR5 Domains Can Mediate Coreceptor Usage by Human Immondeficiency Virus Type 1", *Journal of Virology*, 71(9):6305–6314 (1997).

Osbourn, J., et al., "Directed selection of MIP–1α neutralizing CCR5 antibodies from a phage display human antibody library", *Nature Biotechnology*, 16: 778–781 (1998).

Li, Y., et al., "Antibodies to Human G–Protein Chemokine Receptor HDGNR10 (CCR5 Receptor)", U.S. patent application Publication No.: US2001/0000241A1, Publication Date: Apr. 12, 2001.

Lee, B., et al., "Epitope Mapping of CCR5 Reveals Multiple Conformational States and Distinct but Overlapping Structures Involved n Chemokine and Coreceptor Function", *J. of Biol. Chem.*, 274(14): 9617–9629 (1999).

Hill, C.M., et al., "The Amino Terminous of Human CCR5 is Required for its Functioin as a Receptor for Diverse Human and Simian Immunodeficiency Virus Evelope Glycoproteins", *Virology*, 248: 357–371 (1998).

Olson, W.C., et al. "Differential Inhibition of Human Immunodeficiency Virus Type 1 Fusion, gp120 Binding, and CC–Chemokine Activity by Monoclonal Antibodies to CCR5", *J. of Virology*, 73 (5): 4145–4155 (1999).

Gosling, J., et al., "Molecular uncoupling of C–C chemokine receptor 5–induced chemotaxis and signal transduction from HIV–1 coreceptor activity", *Cell Biology*, 94:5061–5066 (1997).

Frade, Jose M.R., et al., "Characterization of the CCR2 Chemokine Receptor: Functional CCR2 Receptor Expression in B Cells," *J. Immunol.*, 159(11):5576–5584 (1997).

Atchison, R.E., et al., "Multiple Extracellular Elements of CCR5 and HIV–1 Entry: Dissociation from Response to Chemokines", *Science*, 274:1924–1926 (1996).

* cited by examiner

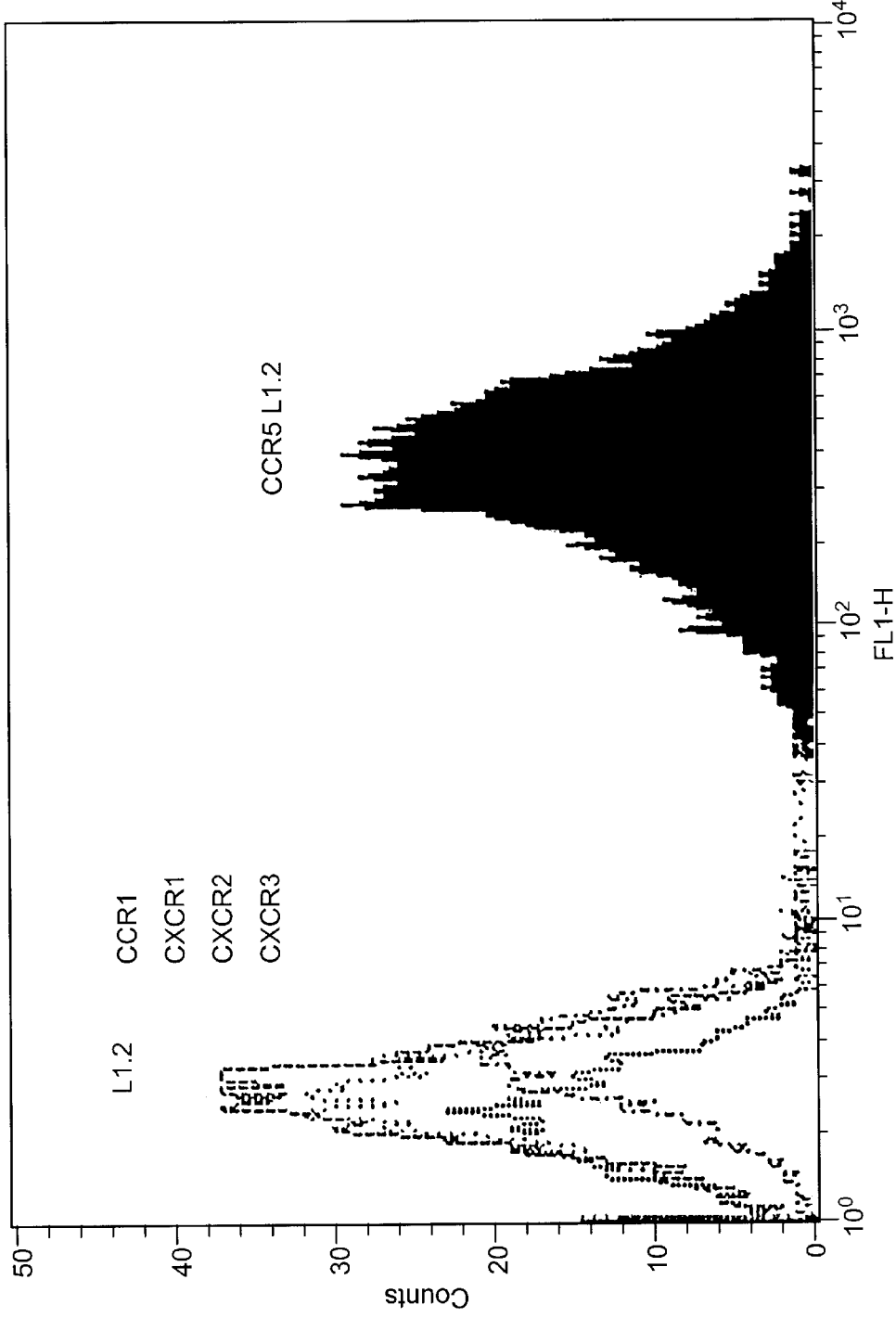

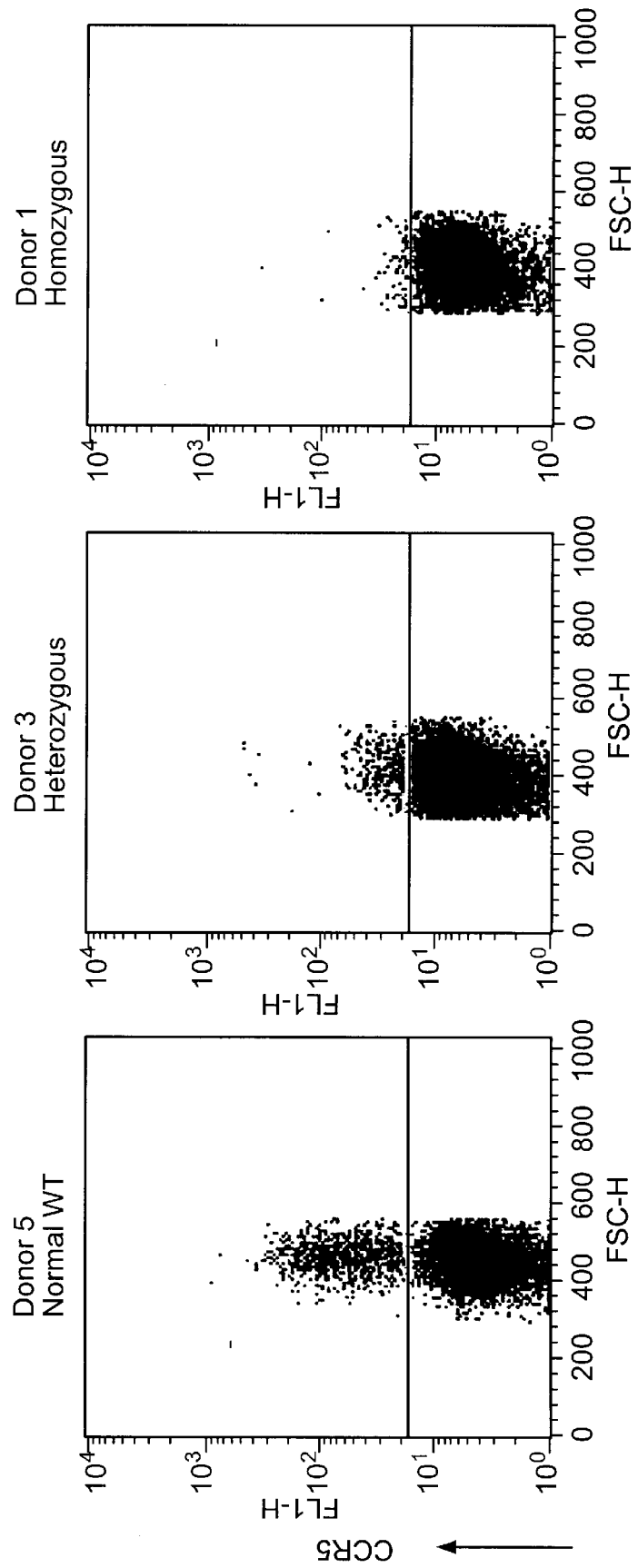

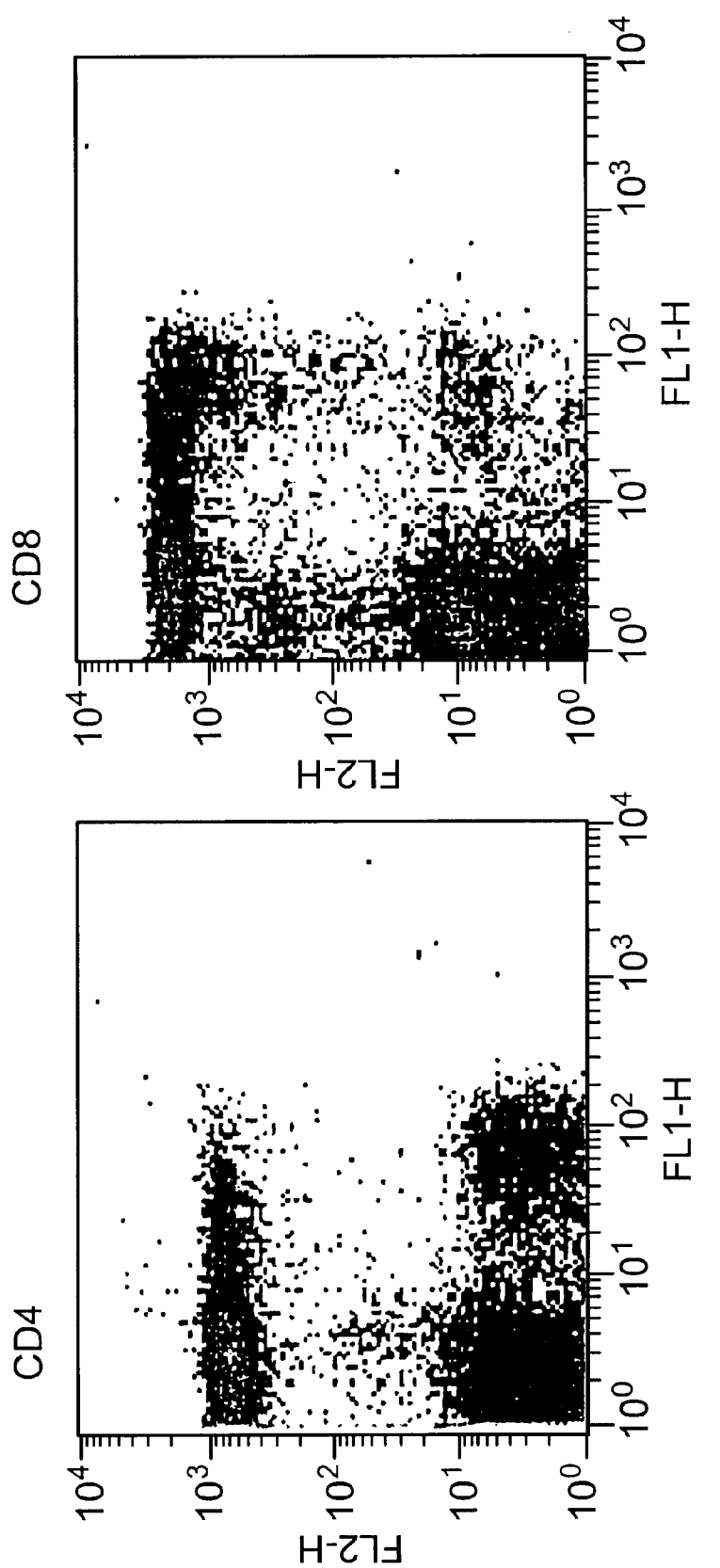

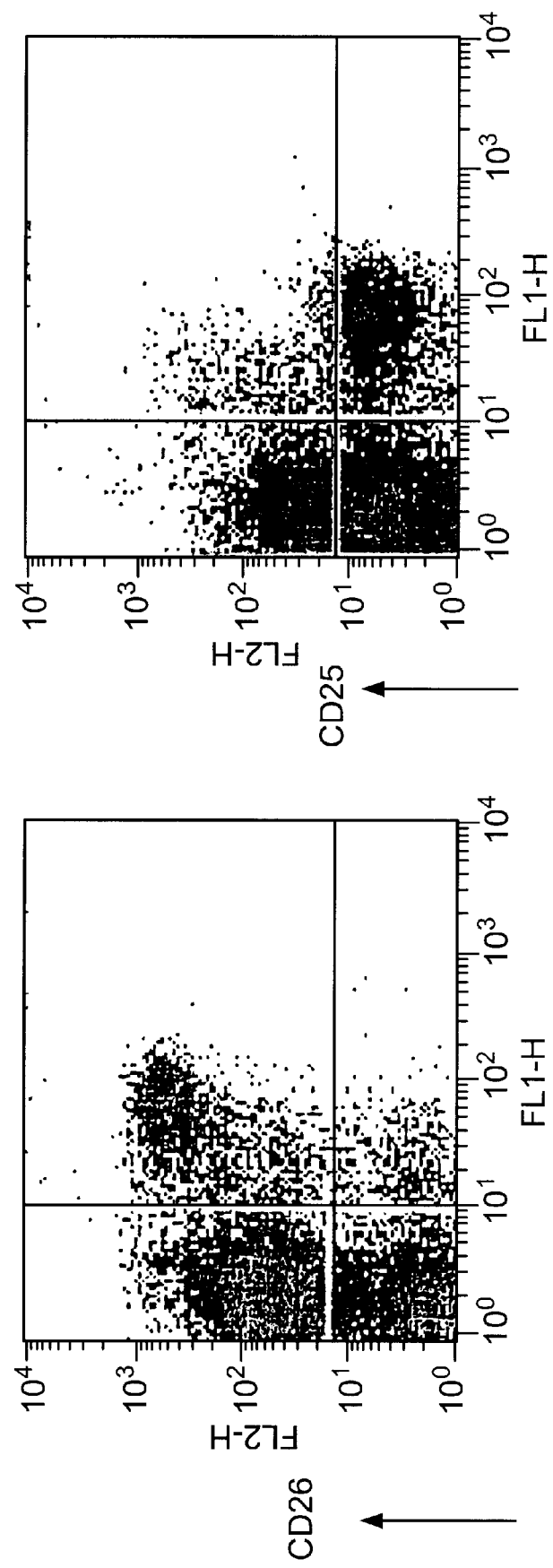

FIG. 7
| | | 3A9 | SC7 | 2D7 | SA11 (CCR2) | 7D9 (CXCR1) |
|---|---|---|---|---|---|---|
| Untransfected | | neg | neg | neg | neg | NO |
| CCR2b |  | neg | neg | neg | + + | neg |
| CCR5 |  | + + | + + | + + | neg | neg |
| C25-01 |  | neg | neg | + + + | + + + | neg |
| C25-06 |  | + + | + + | neg | neg | neg |
| C25-28 | ..PC..  | + + + | + + + | neg | neg | neg |
| C25-17 | Δ2-5  | neg | neg | + + + | neg | neg |
| C25-18 | Δ2-9  | neg | neg | + + + | neg | neg |
| C25-19 | Δ3-13  | neg | neg | + + + | neg | neg |
| C25-20 | Δ2-17  | neg | neg | + + + | neg | neg |
| C25-02 |  | neg | neg | +++ | + + + | neg |
| C25-03 |  | neg | neg | neg | + + + | neg |
| C25-07 |  | + + | + + | neg | neg | neg |
| C25-14 |  | neg | neg | + + | + + | neg |
Antibody Staining

ANTI-CCR5 ANTIBODIES AND KITS COMPRISING SAME

RELATED APPLICATIONS

This application is a continuation-in-part application of U.S. application Ser. No. 08/739,507, filed Oct. 28, 1996 (now abandoned). The teachings of this prior application are incorporated herein by reference in their entirety.

BACKGROUND

Over the past several years a growing family of leukocyte chemoattractant/activating factors, termed chemokines, has been described (Oppenheim, J. J. et al., *Annu. Rev. Immunol.*, 9:617–648 (1991); Schall and Bacon, *Curr. Opin. Immunol.*, 6:865–873 (1994); Baggiolini, M., et al., *Adv. Imunol.*, 55:97–179 (1994)). Members of this family are produced and secreted by many cell types in response to early inflammatory mediators such as IL-1β or TNFα. The chemokine superfamily comprises two main branches: the α-chemokines (or CXC chemokines) and the β-chemokines (CC chemokines). The α-chemokine branch includes proteins such as IL-8, neutrophil activating peptide-2 (NAP-2), melanoma growth stimulatory activity (MGSA/gro or GROα), and ENA-78, each of which have attracting and activating effects predominantly on neutrophils. The members of the β-chemokine branch affect other cell types such as monocytes, lymphocytes, basophils, and eosinophils (Oppenheim, J. J. et al., *Annu. Rev. Immunol.*, 9:617–648 (1991); Baggiolini, M., et al., *Adv. Imunol.*, 55:97–179 (1994); Miller and Krangel, *Crit. Rev. Immunol.*, 12:17–46 (1992); Jose, P. J., et al., *J. Exp. Med.*, 179:881–118 (1994); Ponath, P. D., et al., *J. Clin. Invest.*, 97:604–612 (1996)), and include proteins such as monocyte chemotactic proteins 1–4 (MCP-1, MCP-2, MCP-3, and MCP-4), RANTES, and macrophage inflammatory proteins (MIP-1α, MIP-1β). Recently, a new class of membrane-bound chemokine having a $CX_3C$ motif has been identified (Bazan, J. F. et al., *Nature*, 385: 640–644 (1997)). Chemokines can mediate a range of pro-inflammatory effects on leukocytes, such as chemotaxis, degranulation, synthesis of lipid mediators, and integrin activation (Oppenheim, J. J. et al., *Annu. Rev. Immunol.*, 9:617–648 (1991); Baggiolini, M., et al., *Adv. Imunol.*, 55:97–179 (1994); Miller, M. D. and Krangel, M. S., *Crit. Rev. Immunol.*, 12:17–46 (1992)). Lately, certain β-chemokines have been shown to suppress HIV-1 infection of human T cell lines in vitro (Cocchi, F., et al., *Science* (Wash. DC), 270:1811–1815 (1995)).

Chemokines bind to 7 transmembrane spanning (7TMS) G-protein coupled receptors (Murphy, P. M., *Annu. Rev. Immunol.*, 12:593–633 (1994)). The principal human CXC chemokine receptors characterized to date include: CXCR1 (IL-8 Receptor type A (IL-8 RA)), which binds IL-8; CXCR2 (IL-8 RB), which binds a number of CXC chemokines including IL-8 and GROα (Murphy, P. M. and Tiffany, H. L., *Science* (Wash. DC), 253:1280–3 (1991); Beckmann, M. P., et al., *Biochem. Biophys. Res. Commun.*, 179:784–789 (1991); Holmes, W. E., et al., *Science* (Wash. DC), 253:1278–1280 (1991)); an IP-10/Mig receptor designated CXCR3 (Loetscher et al., *J. Exp. Med.* 184:963–969 (1996)); and CXCR4 (also referred to as "LESTR" or "fusin"), which binds SDF-1 (Nagasawa et al., *Proc. Natl. Acad. Sci. USA* 93:14726–14729 (1996)). The known receptors for the CC or β chemokines Include CCR1, which binds MIP-1α and RANTES (Neote, K., et al., *Cell*, 72:415–425 (1993); Gao, J. L., *J. Exp. Med.*, 177:1421–1427 (1993)); CCR2, which binds MCP-1 and MCP-3 (Charo, I. F., et al., *Proc. Natl. Acad. Sci. USA*, 91:2752–2756 (1994); Myers, S. J., et al., *J. Biol. Chem.*, 270:5786–5792 (1995)); CCR3, which binds chemokines including eotaxin, RANTES and MCP-3 (Ponath, P. D., et al., *J. Exp. Med.*, 183:2437–2448 (1996)); CCR4, which has been found to signal in response to MCP-1, MTP-1α, and RANTES (Power, C. A., et al., *J. Biol. Chem.*, 270:19495–19500 (1995)); and CCR5, which has been shown to signal in response to MIP-1α, MIP-1β and RANTES (Boring, L., et al., *J. Biol. Chem.*, 271 (13):7551–7558 (1996); Raport, C. J., *J. Biol. Chem.*, 271:17161–17166 (1996); and Samson, M. et al., *Biochemistry*, 35:3362–3367 (1996)).

The precise expression of many of the chemokine receptors is not yet known, because specific mAbs are not available. For T cells, PCR or Northern blotting indicates that the known receptors for CC chemokines are expressed on subsets of T cells. Delineating exactly which subsets is an area of intense study, because chemokine receptor expression may explain the localization or migration of various cell types, such as TH1 or TH2 T cells or tissue homing subsets. It may also determine which T cells are infected with different strains of HIV-1. Despite the development of over 130 CD-defined specificities on leukocytes by the [5th] International Leukocyte Workshop in 1993 (Schlossman, S. F., et al., *Leukocyte Typing V*, Oxford University Press, 1995), none of these are specific for chemokine receptors, pointing to the difficulty in making antibodies to these cell surface receptors.

SUMMARY OF THE INVENTION

The present invention relates to an antibody (immunoglobulin) or functional portion thereof (e.g., antigen binding fragment) which binds to a mammalian chemokine receptor 5 protein (also referred to as CKR-5 or CCR5) or portion of the receptor (anti-CCR5). In one embodiment, the antibody of the present invention has specificity for human CCR5 or portion thereof, wherein the antibody blocks binding of a ligand (e.g., RANTES, MIP-1α, MIP-1β, human immunodeficiency virus (HIV)) to the receptor and inhibits function associated with binding of the ligand to the receptor (e.g., leukocyte trafficking). For example, as described herein, antibodies of the present invention having specificity for human CCR5 or a portion thereof, can block binding of a chemokine (e.g., RANTES, MIP-1α, MIP-1β) to the receptor and inhibit function associated with binding of the chemokine to the receptor. In one embodiment, the antibody is monoclonal antibody 5C7 or a monoclonal antibody (mAb) which can compete with 5C7 for binding to human CCR5 or portion of human CCR5. In another embodiment, the antibody is monoclonal antibody 2D7 or a mAb which can compete with 2D7 for binding to human CCR5 or portion of human CCR5.

The present invention further relates to a method of inhibiting the interaction of a cell (e.g., leukocytes, T cells such as CD8+ cells, CD4+ cells and CD45RO+ cells, monocytes and transfected cells) bearing mammalian (e.g., human, non-human primate or murine) CCR5 with a ligand thereof, comprising contacting the cell with an effective amount of an antibody or functional portion thereof which binds to a mammalian CCR5 or portion of CCR5.

Another embodiment of the invention relates to a method of inhibiting the interaction of a cell bearing mammalian chemokine receptor 5 protein with a chemokine, comprising contacting said cell with an effective amount of an antibody or functional portion thereof which binds to a mammalian chemokine receptor 5 protein or portion of said receptor. In one embodiment of the method, the antibody or functional portion thereof is any one or more of 2D7, an antigen binding fragment of 2D7 or an antibody having an epitopic specificity which is the same as or similar to that of 2D7. Furthermore, the invention relates to a method of inhibiting a function associated with binding of a chemokine to the chemokine 5 receptor protein, comprising administering an effective amount of an antibody or functional portion thereof which binds to a mammalian chemokine receptor 5 protein or portion of said receptor. In one aspect of the method, the antibody or functional portion thereof is any one or more of 2D7, an antigen binding fragment of 2D7 or an antibody having an epitopic specificity which is the same as or similar to that of 2D7.

Another aspect of the invention is a method of identifying expression of a mammalian CCR5 or portion of the receptor by a cell. According to the method, a composition comprising a cell or fraction thereof (e.g., a membrane fraction) is contacted with an antibody or functional portion thereof (e.g., 5C7 or 2D7) which binds to a mammalian CCR5 or portion of the receptor under conditions appropriate for binding of the antibody thereto, and the formation of a complex between said antibody and said protein or portion thereof is detected. Detection of the complex indicates the presence of the receptor on the cell. The present invention also relates to a kit for use in detecting the presence of CCR5 or a portion thereof in a biological sample, comprising an antibody or functional portion thereof which binds to a mammalian chemokine receptor 5 protein or portion of said receptor, and ancillary reagents suitable for detecting the presence of a complex between said antibody and said protein or portion thereof.

Also encompassed by the present invention are methods of identifying additional ligands or other substances which bind a mammalian CCR5 protein, including inhibitors and/ or promoters of mammalian CCR5 function. For example, agents having the same or a similar binding specificity as that of an antibody of the present invention or functional portion thereof can be identified by a competition assay with said antibody or portion thereof. Thus, the present invention also encompasses methods of identifying ligands or other substances which bind the CCR5 receptor, including inhibitors (e.g., antagonists) or promoters (e.g., agonists) of receptor function. In one embodiment, suitable host cells which have been engineered to express a receptor protein or variant encoded by a nucleic acid introduced into said cells are used in an assay to identify and assess the efficacy of ligands, inhibitors or promoters of receptor function. Such cells are also useful in assessing the function of the expressed receptor protein or polypeptide.

Thus, the invention also relates to a method of detecting or identifying an agent which binds a mammalian chemokine receptor 5 protein or ligand binding variant thereof, comprising combining an agent to be tested, an antibody or antigen binding fragment of the present invention (e.g., 2D7, an antibody having an epitopic specificity which is the same as or similar to that of 2D7, and antigen binding fragments thereof) and a composition comprising a mammalian chemokine receptor 5 protein or a ligand binding variant thereof. The foregoing components can be combined under conditions suitable for binding of the antibody or antigen binding fragment to mammalian chemokine receptor 5 protein or a ligand binding variant thereof, and binding of the antibody or fragment to the mammalian chemokine receptor 5 protein or ligand binding variant is detected or measured, either directly or indirectly, according to methods described herein or other suitable methods. A decrease in the amount of complex formed relative to a suitable control (e.g., in the absence of the agent to be tested) is indicative that the agent binds said receptor or variant. The composition comprising a mammalian chemokine receptor 5 protein or a ligand binding variant thereof can be a membrane fraction of a cell bearing recombinant chemokine receptor 5 protein or ligand binding variant thereof. The antibody or fragment thereof can be labeled with a label such as a radioisotope, spin label, antigen label, enzyme label, fluorescent group and chemiluminescent group. These and similar assays can be used to detect agents, including ligands (e.g., chemokines or strains of HIV which interact with CCR5) or other substances, including inhibitors or promoters of receptor function, which can bind CCR5 and compete with the antibodies described herein for binding to the receptor.

According to the present invention, ligands, inhibitors or promoters of receptor function can be identified in a suitable assay, and further assessed for therapeutic effect. Inhibitors of receptor function can be used to inhibit (reduce or prevent) receptor activity, and ligands and/or promoters can be used to induce (trigger or enhance) normal receptor function where indicated. Thus, the present invention also provides a method of treating HIV or inflammatory diseases, including autoimmune disease and graft rejection, comprising administering an inhibitor of receptor function to an individual (e.g., a mammal). The present invention further provides a method of stimulating receptor function by administering a novel ligand or promoter to an individual, providing a new approach to selective stimulation of leukocyte function, which is useful, for example, in the treatment of infectious diseases and cancer.

The present invention also relates to a method of detecting the susceptibility of a mammal to HIV. According to the method, a sample to be tested is contacted with an antibody or functional portion thereof which binds to a mammalian CCR5 or portion thereof, under conditions appropriate for binding of said antibody thereto, wherein the sample comprises cells which express CCR5 in normal individuals. Binding of antibody is detected using a suitable assay, and the binding of the antibody is indicative of the level of receptor expressed by the cells, which correlates with the susceptibility of the mammal to HIV. Thus, the method can be used to determine the expression level of CCR5 on the T cells of a susceptible but uninfected individual to determine the degree of risk to such an individual upon exposure to HIV. In another embodiment, a sample comprising a mammalian CCR5 protein, such as a cellular fraction or liposomes comprising said protein, can be used.

The present invention also encompasses a method of determining the prognosis for HIV in a mammal. According to the method, a sample to be tested is contacted with an antibody or functional portion thereof which binds to a mammalian CCR5 or portion thereof, under conditions appropriate for binding of said antibody thereto, wherein the sample comprises cells which express CCR5 in normal individuals. Binding of antibody is detected, and binding of antibody is indicative of the level of receptor expressed by the cells, which correlates with the prognosis for HIV in the mammal. In another embodiment, a sample comprising a mammalian CCR5 protein, such as a cellular fraction or liposomes comprising said protein, can be used.

Another aspect of the invention relates to a method of inhibiting HIV infection of a cell which expresses a mammalian CCR5 or portion thereof (e.g., monocytes, macrophages, dendritic cells or T cells such as CD4+ cells, CD8+ cells), comprising contacting the cell with an effective amount of an antibody or functional portion thereof which binds to a mammalian CCR5 or portion of the receptor.

Also encompassed by the present invention is a method of inhibiting (e.g., treating) HIV in a patient, comprising administering to the patient an effective amount of an antibody or functional portion thereof which binds to a mammalian CCR5 or portion of said receptor.

Another aspect of the invention also relates to a method of preventing or inhibiting HIV infection in an individual, comprising administering to the individual an effective amount of an antibody or functional portion thereof which binds to CCR5. According to the method, preventing HIV infection includes treatment in order to prevent (reduce or eliminate) infection of new cells in an infected individual or in order to prevent infection in an individual who may be, may have been or has been exposed to HIV. For example, individuals such as an HIV infected individual, a fetus of an HIV infected female, or a health care worker can be,treated according to the method of the present invention.

The present invention also encompasses a method of inhibiting leukocyte trafficking in a patient, comprising administering to the patient an effective amount of an antibody or functional portion thereof which binds to a mammalian CCR5 or portion of said receptor.

BRIEF DESCRIPTION OF THE FIGURES

FIG. 1 is a FACScan® profile illustrating that mAb 5C7 is reactive with CCR5 transfected L1.2 cells (solid lines), but not with L1.2 cells transfected with a variety of other chemokine receptors (broken lines).

FIGS. 2A–2C are FACScan® dot plots in which expression of CCR5 on lymphocytes from a normal individual (Donor 5) (FIG. 2A), an individual heterozygous for the CCR5 deletion (Donor 3) (FIG. 2B), and an individual homozygous for the CCR5 deletion (Donor 1) (FIG. 2C) was monitored. Staining was performed using PBMC, and cells were gated so that the lymphocyte population was assessed. The X-axis represents forward light scatter (a measure of cell size), and the Y-axis fluorescence intensity of staining for CCR5 (using mAb 5C7, and a second step anti-mouse Ig-FITC). The level of negative control staining is indicated by a line.

FIG. 3A shows the position of the CCR5 deletion, and the sequence difference between the normal (CCR5 wild type (WT), SEQ ID NO:1) and mutant (CCR5 MUT, SEQ ID NO:2) forms of CCR5. FIG. 3B is a photograph of an agarose gel demonstrating the bands detected in normal CCR5 individuals (Donor 5), homozygous CCR5 mutant individuals (Donors 1 and 2), and CCR5 heterozygous individuals (Donors 3 and 4). Genomic DNA was isolated from PBMC cells of selected blood donors. PCR reactions were carried out using a set of 5' and 3' primers, the reaction products were run on a 4% Nusieve GTG agarose gel and DNA bands stained by ethidium bromide. Under these conditions, a 174-bp band for a normal individual, a 142-bp band for homozygous CCR5 mutant individuals, and both 174-bp and 142-bp bands for CCR5 heterozygous individuals were detected.

FIGS. 4A–4B are FACScan® dot plots assessing expression of CCR5 on CD4+ (FIG. 4A) and CD8+. (FIG 4B) cells, although CCR5 was expressed preferentially on the CD8+ subset.

FIGS. 5A–5D are FACScan® dot plots assessing expression of CCR5 on memory lymphocytes (FIGS. 5A–5B) and activated lymphocytes (FIGS. 5C-5D). Human PBMC were stained with mAb 5C7, followed by anti-mouse Ig-FITC, and were then stained for CD45RO (FIG. 5a), and CD45A (FIG. 5B), CD26 (FIG. 5C), or CD25 (IL-2R) (FIG. 5D), using PE-labeled mAbs (Becton Dickinson). As indicated, CCR5 was largely absent from the IL-2 receptor (IL-2R) subset. FL1 (green fluorescence, 5C7 staining in all plots is shown on the X-axis, and FL2 (red fluorescence) is shown on the Y-axis. The PE-labeled mAb used (FL2 staining) is indicated for each plot.

FIG. 6A illustrates the reactivity of mAb 2D7 with CCR5 L1.2 cells, but not with CXCR4 L1.2 cells. FIG. 6B illustrates the results of two color staining of human PBL with 2D7 (green fluorescence) and 12G5 (anti-CXCR4, red fluorescence). Quadrants were set on the basis of control and single color staining.

FIG. 7 illustrates the reactivity of CCR5-specific mAbs with cells expressing various CCR5/CCR2b receptor chimeras or untransfected control cells. The structures of CCR5/CCR2b chimeras used are shown schematically on the left hand side. Regions derived from CCR5 are shown as shadded regions, and regions derived from CCR2b are shown as dark lines. Stable CHO cell transfectants expressing various CCR5CCR2b receptor chimeras were stained with anti-CCR5 mAb 3A9, 5C7, 2D7, anti-CCR2b mAb 5A.1, or anti-CXCR1 mAb 7D9. Level of staining of the transfectants by the various mAbs was graded + to +++, or negative (neg).

In FIG. 9A, an irrelevant mAb (MOPC-21) was used, and in FIG. 9B, mAb 2D7 was used. Antibodies were used at a final concentration of 20 μg/ml. MIP-1α was used at 100 nM, and SDF-1 was used at 200 nM.

FIG. 10A shows CCR5 L1.2 cell chemotaxis; FIG. 10B shows blood lymphocyte chemotaxis; FIG. 10C shows blood monocyte chemotaxis; and FIG. 10D shows day 21 activated, IL-2 stimulated T cell (CD3 blast) chemotaxis. The results are representative of at least four separate experiments. The chemotactic indices for MIP-1β treated cells (open circles), RANTES treated cells (open squares), and MIP-1α treated cells (open diamonds), were calculated by dividing the number of migrated cells for a specific chemokine by the "no chemoklne" background value.

FIG. 11A is a graph illustrating inhibition of radiolabeled M-tropic HIV-1 JRFL gp120 binding to CCR5 L1.2 transfectants by mAb 2D7 or mAb 3A9. 100% of inhibition was defined as the level of inhibition achieved in the presence of 100 nM unlabeled gp120. The percent inhibition achieved by mAb 2D7 (open circles), mAb 3A9 (filled triangles) or IgG1 (open squares), is shown. FIG. 11B is a bar graph illustrating inhibition of HIV-1 infection in U87-CD4-CCR5 cells by mAb 2D7. The infectability of U87-CD4-CCR5 cells by macrophage-tropic (ADA and JRFL), dual-tropic (DH123) and T-tropic (HxB) HIV-1 strains, in the absence or presence of increasing concentrations of 2D7 or an IgG1 control mAb, was determined using a virus entry assay. Infection of the cells was measured by quantification of luciferase activity.

DETAILED DESCRIPTION

Figure 3A:
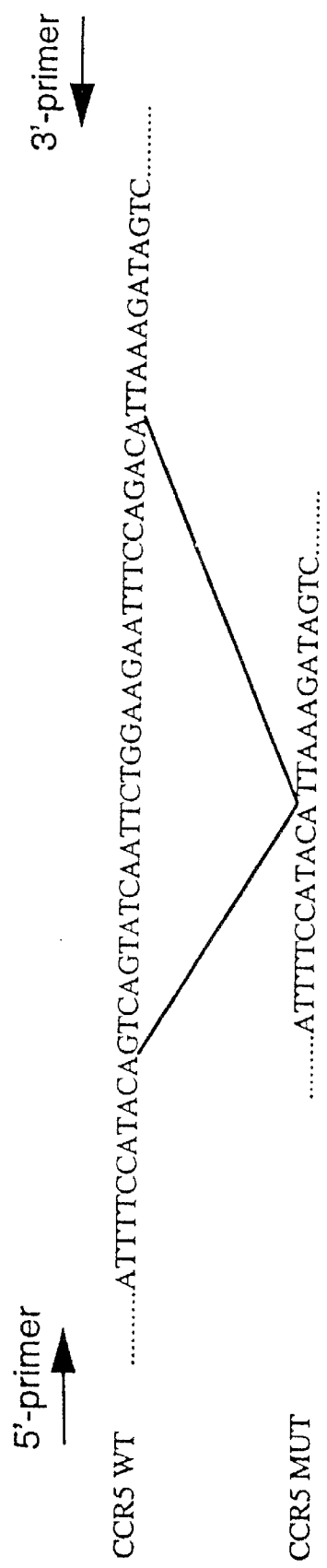
FIGS. 3A–3B illustrate the position of the CCR5 deletion and the presence or absence of mutant CCR5 alleles in various individuals.

The present invention relates to an antibody (anti-CCR5) having binding specificity for mammalian chemokine receptor 5 protein (CKR-5 or CCR5) or a portion of CCR5. In one embodiment, the antibodies (immunoglobulins) are raised against an isolated and/or recombinant mammalian CCR5 or portion thereof (e.g., peptide) or against a host cell which expresses recombinant mammalian CCR5. In a preferred embodiment, the antibodies specifically bind human CCR5 receptor(s) or a portion thereof, and in a particularly preferred embodiment the antibodies have specificity for a naturally occurring or endogenous human CCR5. Antibodies which can inhibit one or more functions characteristic of a mammalian CCR5, such as a binding activity (e.g., ligand, inhibitor and/or promoter binding), a signalling activity (e.g., activation of a mammalian G protein, induction of a rapid and transient increase in the concentration of cytosolic free calcium $[Ca^{2+}]i$), and/or stimulation of a cellular response (e.g., stimulation of chemotaxis, exocytosis or inflammatory mediator release by leukocytes, integrin activation) are also encompassed by the present invention, such as an antibody which can inhibit binding of a ligand (i.e., one or more ligands) to CCR5 and/or one or more functions mediated by CCR5 in response to a ligand. For example, in one aspect, the antibodies can inhibit (reduce or prevent) the interaction of receptor with a natural ligand, such as RANTES, MIP-1α and/or MIP-1β. In another aspect, a monoclonal antibody that reacts with CCR5 can inhibit binding of RANTES, MIP-1α, MIP-1β and/or HIV to mammalian CCR5 (e.g., human CCR5, non-human primate CCR5, murine CCR5). Monoclonal antibody directed against CCR5 can inhibit functions mediated by human CCR5, including leukocyte trafficking, HIV entry into a cell, T cell activation, inflammatory mediator release and/or leukocyte degranulation. Preferably, the immunoglobulins can bind CCR5 with an affinity of at least about $1\times10^{-9}$ M, and preferably at least about $3\times10^{-9}$ M.

Murine monoclonal antibodies specific for CCR5 of human origin, designated 5C7 and 2D7, were produced as described herein. In a particular embodiment, the antibodies of the present invention have specificity for human CCR5, and have an epitopic specificity which is the same as or similar to that of murine 5C7 or 2D7 antibody described herein. Antibodies with an epitopic specificity similar to that of murine 5C7 monoclonal antibody can be identified by their ability to compete with murine 5C7 monoclonal antibody for binding to human CCR5 (e.g., to cells bearing human CCR5, such as transfectants bearing CCR5 (see Example 1), CD8+ cells, CD4+ cells, CDR45RO+ cells, monocytes, dendritic cells, macrophages). Similarly, antibodies with an epitopic specificity which is the same as or similar to that of murine 2D7 monoclonal antibody can be identified by their ability to compete with murine 2D7 monoclonal antibody for binding to human CCR5. Using receptor chimeras, the binding site of mAb 2D7 has been mapped to the second extracellular domain of CCR5. Using these or other suitable techniques, antibodies having an epitopic specificity which is the same as or similar to that of an antibody of the present invention can be identified. mAb 5C7, like mAb 3A9, has epitopic specificity for the amino-terminus of the CCR5 receptor. mAb 2D7 has epitopic specificity for the second extracellular loop of the CCR5 receptor. Thus, the invention pertains to an antibody or functional portion thereof which binds to a second extracellular loop or portion thereof of mammalian chemokine receptor 5 protein, or which binds to the amino-terminal region or portion thereof of mammalian chemokine receptor 5 protein.

The invention also relates to a bispecific antibody, or functional portion thereof, which has the same or similar epitopic specificity as at least two of the antibodies described herein (see, e.g., U.S. Pat. No. 5,141,736 (Iwasa et al.), U.S. Pat. Nos. 4,444,878, 5,292,668, 5,523,210 (all to Paulus et al.) and U.S. Pat. No. 5,496,549 (Yamazaki et al.). For example, a bispecific antibody of the present invention can have the same or similar epitopic specificity as mAb 2D7 and 5C7, e.g., binds the second extracellular loop, or portion thereof, and the amino terminal region, or portion thereof, of mammalian CCR5 protein.

The present invention also pertains to the hybridoma cell lines deposited under ATCC Accession No. HB-12222 and ATCC Accession No. HB-12366, at the American Type Culture Collection, 10801 University Boulevard, Manassas, Va. 20110-2209, on Oct. 25, 1996 and Jun. 6, 1997, respectively, as well as to the monoclonal antibodies produced by the hybridoma cell lines deposited under ATCC Accession Nos. HB-12222 and HB-12366.

The antibodies of the present invention can be polyclonal or monoclonal, and the term "antibody" is intended to encompass both polyclonal and monoclonal antibodies. Furthermore, it is understood that methods described herein which utilize 2D7 can also utilize antigen binding fragments of 2D7, antibodies which have the same or similar epitopic specificity as 2D7, and combinations thereof, optionally in combination with antibodies having an epitopic specificity which is not the same as or similar to 2D7; similarly, methods described as utilizing 5C7 can also utilize antigen binding fragments of 5C7, antibodies which have the same or similar epitopic specificity as 5C7, and combinations thereof, optionally in combination with antibodies having an epitopic specificity which is not the same as or similar to 2D7. Antibodies of the present invention can be raised against an appropriate immunogen, such as isolated and/or recombinant mammalian CCR5 protein or portion thereof, or synthetic molecules, such as synthetic peptides. In a preferred embodiment, cells which express receptor, such as transfected cells, can be used as immunogens or in a screen for antibody which binds receptor.

The antibodies of the present invention, and fragments thereof, are useful in therapeutic, diagnostic and research applications as described herein. The present invention encompasses an antibody or functional portion thereof of the present invention (e.g., mAb 2D7 or 5C7, or antigen-binding fragments thereof) for use in therapy (including prophylaxis) or diagnosis (e.g., of particular diseases or conditions as described herein), and use of such antibodies or functional portions thereof for the manufacture of a medicament for use in treatment of diseases or conditions as described herein.

Preparation of immunizing antigen, and polyclonal and monoclonal antibody production can be performed as described herein, or using other suitable techniques. A variety of methods have been described (see e.g., Kohler et al., *Nature,* 256: 495–497 (1975) and *Eur. J. Immunol.* 6: 511–519 (1976); Milstein et al., *Nature* 266: 550–552 (1977); Koprowski et al., U.S. Pat. No. 4,172,124; Harlow, E. and D. Lane, 1988, *Antibodies: A Laboratory Manual,* (Cold Spring Harbor Laboratory: Cold Spring Harbor, N.Y.); *Current Protocols In Molecular Biology,* Vol. 2 (Supplement 27, Summer '94), Ausubel, F. M. et al., Eds., (John Wiley & Sons: New York, N.Y.), Chapter 11, (1991)). Generally, a hybridoma can be produced by fusing a suitable immortal cell line (e.g., a myeloma cell line such as SP2/0) with antibody producing cells. The antibody producing cell, preferably those of the spleen or lymph nodes, are obtained from animals immunized with the antigen of interest. The fused cells (hybridomas) can be isolated using selective culture conditions, and cloned by limiting dilution. Cells which produce antibodies with the desired specificity can be selected by a suitable assay (e.g., ELISA).

Other suitable methods of producing or isolating antibodies of the requisite specificity can used, including, for example, methods which select recombinant antibody from a library, or which rely upon immunization of transgenic animals (e.g., mice) capable of producing a full repertoire of human antibodies (see e.g., Jakobovits et al., *Proc. Natl. Acad. Sci. USA,* 90: 2551–2555 (1993); Jakobovits et al., *Nature,* 362: 255–258 (1993); Lonberg et al., U.S. Pat. No. 5,545,806; Surani et al., U.S. Pat. No. 5,545,807).

Single chain antibodies, and chimeric, humanized or primatized (CDR-grafted) antibodies, as well as chimeric or CDR-grafted single chain antibodies, comprising portions derived from different species, are also encompassed by the present invention and the term "antibody". The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; and Winter, European Patent No. 0,239,400 B1. See also, Newman, R. et al., *BioTechnology,* 10: 1455–1460 (1992), regarding primatized antibody, and Ladner et al., U.S. Pat. No. 4,946,778 and Bird, R. E. et al., *Science,* 242: 423–426 (1988)) regarding single chain antibodies.

In addition, functional fragments of antibodies, including fragments of chimeric, humanized, primatized or single chain antibodies, can also be produced. Functional fragments of the foregoing antibodies retain at least one binding function and/or modulation function of the full-length antibody from which they are derived. Preferred functional fragments retain an antigen binding function of a corresponding full-length antibody (e.g., specificity for a mammalian CCR5). Particularly preferred functional fragments retain the ability to inhibit one or more functions characteristic of a mammalian CCR5, such as a binding activity, a signalling activity, and/or stimulation of a cellular response. For example, in one embodiment, a functional fragment can inhibit the interaction of CCR5 with one or more of its ligands (e.g., RANTES, MIP-1α, MIP-1β, HIV) and/or can inhibit one or more receptor-mediated functions, such as leukocyte trafficking, HIV entry into cells, T cell activation, inflammatory mediator release and/or leukocyte degranulation.

For example, antibody fragments capable of binding to a mammalian CCR5 receptor or portion thereof, including, but not limited to, Fv, Fab, Fab' and F(ab')$_2$ fragments are encompassed by the invention. Such fragments can be produced by enzymatic cleavage or by recombinant techniques. For instance, papain or pepsin cleavage can generate Fab or F(ab')$_2$ fragments, respectively. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH$_1$ domain and hinge region of the heavy chain.

The term "humanized immunoglobulin" as used herein refers to an immunoglobulin comprising portions of immunoglobulins of different origin, wherein at least one portion is of human origin. Accordingly, the present invention relates to a humanized immunoglobulin having binding specificity for a mammalian CCR5 (e.g., human CCR5, murine CCR5), said immunoglobulin comprising an antigen binding region of nonhuman origin (e.g., rodent) and at least a portion of an immunoglobulin of human origin (e.g., a human framework region, a human constant region or portion thereof). For example, the humanized antibody can comprise portions derived from an immunoglobulin of nonhuman origin with the requisite specificity, such as a mouse, and from immunoglobulin sequences of human origin (e.g., a chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin of the present invention is an immunoglobulin containing one or more immunoglobulin chains comprising a CDR of nonhuman origin (e.g., one or more CDRs derived from an antibody of nonhuman origin) and a framework region derived from a light and/or heavy chain of human origin (e.g., CDR-grafted antibodies with or without framework changes). In one embodiment, the humanized immunoglobulin can compete with murine 5C7 or 2D7 monoclonal antibody for binding to human CCR5. In a preferred embodiment, the antigen binding region of the humanized immunoglobulin (a) is derived from 5C7 monoclonal antibody (e.g., as in a humanized immunoglobulin comprising CDR1, CDR2 and CDR3 of the 5C7 light chain and CDR1, CDR2 and CDR3 of the 5C7 heavy chain) or (b) is derived from 2D7 monoclonal antibody (e.g., as in a humanized immunoglobulin comprising CDR1, CDR2 and CDR3 of the 2D7 light chain and CDR1, CDR2 and CDR3 of the 2D7 heavy chain). Chimeric or CDR-grafted single chain antibodies are also encompassed by the term humanized immunoglobulin. See, e.g., Cabilly et al., U.S. Pat. No. 4,816,567; Cabilly et al., European Patent No. 0,125,023 B1; Queen et al., European Patent No. 0,451,216 B1; Boss et al., U.S. Pat. No. 4,816,397; Boss et al., European Patent No. 0,120,694 E1; Neuberger, M. S. et al., WO 86/01533; Neuberger, M. S. et al., European Patent No. 0,194,276 B1; Winter, U.S. Pat. No. 5,225,539; winter, European Patent No. 0,239,400 B1; Padlan, E. A. et al., European Patent Application No. 0,519, 596 A1. See also, Ladner et al., U.S. Pat. No. 4,946,778; Huston, U.S. Pat. No. 5,476,786; and Bird, R. E. et al., *Science,* 242: 423–426 (1988)), regarding single chain antibodies.

Such humanized immunoglobulins can be produced using synthetic and/or recombinant nucleic acids to prepare genes (e.g., cDNA) encoding the desired humanized chain. For example, nucleic acid (e.g., DNA) sequences coding for humanized variable regions can be constructed using PCR mutagenesis methods to alter DNA sequences encoding a human or humanized chain, such as a DNA template from a previously humanized variable region (see e.g., Kamman, M., et al., *Nucl. Acids Res.*, 17: 5404 (1989)); Sato, K., et al., *Cancer Research*, 53: 851–856 (1993); Daugherty, B. L. et al., *Nucleic Acids Res.*, 19(9): 2471–2476 (1991); and Lewis, A. P. and J. S. Crowe, Gene, 101: 297–302 (1991)). Using these or other suitable methods, variants can also be readily produced. In one embodiment, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993)).

The present invention also pertains to the hybridoma cell lines deposited under ATCC Accession Nos. HB-12222 and HB-12366, as well as to the monoclonal antibodies produced by the hybridoma cell lines deposited under ATCC Accession Nos. HB-12222 and HB-12366. The cell lines of the present invention have uses other than for the production of the monoclonal antibodies. For example, the cell lines of the present invention can be fused with other cells (such as suitably drug-marked human myeloma, mouse myeloma, human-mouse heteromyeloma or human lymphoblastoid cells) to produce additional hybridomas, and thus provide for the transfer of the genes encoding the monoclonal antibodies. In addition, the cell lines can be used as a source of nucleic acids encoding the anti-CCR5 immunoglobulin chains, which can be isolated and expressed (e.g., upon transfer to other cells using any suitable technique (see e.g., Cabilly et al., U.S. Pat. No. 4,816,567; Winter, U.S. Pat. No. 5,225,539)). For instance, clones comprising a rearranged anti-CCR5 light or heavy chain can be isolated (e.g., by PCR) or cDNA libraries can be prepared from mRNA isolated from the cell lines, and cDNA clones encoding an anti-CCR5 immunoglobulin chain can be isolated. Thus, nucleic acids encoding the heavy and/or light chains of the antibodies or portions thereof can be obtained and used in accordance with recombinant DNA techniques for the production of the specific immunoglobulin, immunoglobulin chain, or variants thereof (e.g., humanized immunoglobulins) in a variety of host cells or in an in vitro translation system. For example, the nucleic acids, including cDNAs, or derivatives thereof encoding variants such as a humanized immunoglobulin or immunoglobulin chain, can be placed into suitable prokaryotic or eukaryotic vectors (e.g., expression vectors) and introduced into a suitable host cell by an appropriate method (e.g., transformation, transfection, electroporation, infection), such that the nucleic acid is operably linked to one or more expression control elements (e.g., in the vector or integrated into the host cell genome). For production, host cells can be maintained under conditions suitable for expression (e.g., in the presence of inducer, suitable media supplemented with appropriate salts, growth factors, antibiotic, nutritional supplements, etc.), whereby the encoded polypeptide is produced. If desired, the encoded protein can be recovered and/or isolated (e.g., from the host cells, medium, milk). It will be appreciated that the method of production encompasses expression in a host cell of a transgenic animal (see e.g., WO 92/03918, GenPharm International, published Mar. 19, 1992).

As described herein, antibodies of the present invention can block (inhibit) binding of a ligand to CCR5 and/or inhibit function associated with binding of the ligand to the CCR5. As discussed below various methods can be used to assess inhibition of binding of a ligand to CCR5 and/or function associated with binding of the ligand to the receptor.

Binding Assays

As used herein "mammalian CCR5 protein" refers to naturally occurring or endogenous mammalian CCR5 proteins and to proteins having an amino acid sequence which is the same as that of a naturally occurring or endogenous corresponding mammalian CCR5 protein (e.g., recombinant proteins). Accordingly, as defined herein, the term includes mature receptor protein, polymorphic or allelic variants, and other isoforms of a mammalian CCR5 (e.g., produced by alternative splicing or other cellular processes), and modified or unmodified forms of the foregoing (e.g., glycosylated, unglycosylated). Mammalian CCR5 proteins can be isolated and/or recombinant proteins (including synthetically produced proteins). Naturally occurring or endogenous mammalian CCR5 proteins include wild type proteins such as mature CCR5, polymorphic or allelic variants and other isoforms which occur naturally in mammals (e.g., humans, non-human primates). Such proteins can be recovered or isolated from a source which naturally produces mammalian CCR5, for example. These proteins and mammalian CCR5 proteins having the same amino acid sequence as a naturally occurring or endogenous corresponding mammalian CCR5, are referred to by the name of the corresponding mammal. For example, where the corresponding mammal is a human, the protein is designated as a human CCR5 protein (e.g., a recombinant human CCR5 produced in a suitable host cell).

"Functional variants" of mammalian CCR5 proteins include functional fragments, functional mutant proteins, and/or functional fusion proteins (e.g., produced via mutagenesis and/or recombinant techniques). Generally, fragments or portions of mammalian CCR5 proteins include those having a deletion (i.e., one or more deletions) of an amino acid (i.e., one or more amino acids) relative to the mature mammalian CCR5 protein (such as N-terminal, C-terminal or internal deletions). Fragments or portions in which only contiguous amino acids have been deleted or in which non-contiguous amino acids have been deleted relative to mature mammalian CCR5 protein are also envisioned.

Generally, mutants of mammalian CCR5 proteins include natural or artificial variants of a mammalian CCR5 protein differing by the addition, deletion and/or substitution of one or more contiguous or non-contiguous amino acid residues (e.g., receptor chimeras). Such mutations can be in a conserved region or nonconserved region (compared to other CXC and/or CC chemokine receptors), extracellular, cytoplasmic, or transmembrane region, for example.

A "functional fragment or portion", "functional mutant" and/or "functional fusion protein" of a mammalian CCR5 protein refers to an isolated and/or recombinant protein or polypeptide which has at least one function characteristic of a mammalian CCR5 protein as described herein, such as a binding activity, a signalling activity and/or ability to stimulate a cellular response. Preferred functional variants can bind a ligand (i.e., one or more ligands such as MIP-1α, MIP-1β, RANTES, HIV), and are referred to herein as "ligand binding variants".

A composition comprising an isolated and/or recombinant mammalian CCR5 or portion thereof can be maintained under conditions suitable for binding, the receptor is contacted with an antibody to be tested, and binding is detected or measured. In one embodiment, a receptor protein can be expressed in cells which naturally express CCR5 or in cells stably or transiently transfected with a construct comprising a nucleic acid sequence which encodes a mammalian CCR5 or portion thereof. The cells are maintained under conditions appropriate for expression of receptor. The cells are contacted with an antibody under conditions suitable for binding (e.g., in a suitable binding buffer), and binding is detected by standard techniques. To measure binding, the extent of binding can be determined relative to a suitable control (e.g., compared with background determined in the absence of antibody, compared with binding of a second antibody (i.e., a standard), compared with binding of antibody to untransfected cells). A cellular fraction, such as a membrane fraction, containing receptor or liposomes comprising receptor can be used in lieu of whole cells.

In one embodiment, the antibody is labeled with a suitable label (e.g., fluorescent label, isotope label, enzyme label), and binding is determined by detection of the label. In another embodiment, bound antibody can be detected by labeled second antibody. Specificity of binding can be assessed by competition or displacement, for example, using unlabeled antibody or a ligand as competitor.

Binding inhibition assays can also be used to identify antibodies which bind CCR5 and inhibit binding of another compound such as a ligand (MIP-1α, MIP-1 β, RANTES). For example, a binding assay can be conducted in which a reduction in the binding of a ligand of CCR5 (in the absence of an antibody), as compared to binding of the ligand in the presence of the antibody, is detected or measured. The receptor can be contacted with the ligand and antibody simultaneously, or one after the other, in either order. A reduction in the extent of binding of the ligand in the presence of the antibody, is indicative of inhibition of binding by the antibody. For example, binding of the ligand could be decreased or abolished.

In one embodiment, direct inhibition of the binding of a ligand (e.g., a chemokine such as RANTES) to a mammalian CCR5 by an antibody is monitored. For example, the ability of an antibody to inhibit the binding of $^{125}$I-labeled RANTES, $^{125}$I-labeled MIP-1α or $^{125}$I-labeled MIP-1β to mammalian CCR5 can be monitored. Such an assay can be conducted using either whole cells (e.g., T cells, or a suitable cell line containing nucleic acid encoding a mammalian CCR5) or a membrane fraction from said cells, for instance.

Other methods of identifying the presence of an antibody which binds CCR5 are available, such as other suitable binding assays, or methods which monitor events which are triggered by receptor binding, including signalling function and/or stimulation of a cellular response (e.g., leukocyte trafficking).

It will be understood that the inhibitory effect of antibodies of the present invention can be assessed in a binding inhibition assay. Competition between antibodies for receptor binding can also be assessed in the method. Antibodies which are identified in this manner can be further assessed to determine whether, subsequent to binding, they act to inhibit other functions of CCR5 and/or to assess their therapeutic utility.

Signalling Assays

The binding of a ligand or promoter, such as an agonist, to CCR5 can result in signalling by a G protein-coupled receptor, and the activity of G proteins is stimulated. The induction of signalling function by a compound can be monitored using any suitable method. Such an assay can be used to identify antibody agonists of CCR5. The inhibitory activity of an antibody can be determined using a ligand or promoter in the assay, and assessing the ability of the antibody to inhibit the activity induced by ligand or promoter.

G protein activity, such as hydrolysis of GTP to GDP, or later signalling events triggered by receptor binding, such as induction of rapid and transient increase in the concentration of intracellular (cytosolic) free calcium $[Ca^{2+}]_i$, can be assayed by methods known in the art or other suitable methods (see e.g., Neote, K. et al., *Cell,* 72: 415–425 1993); Van Riper et al., *J. Exp. Med.,* 177: 851–856 (1993); Dahinden, C. A. et al., *J. Exp. Med.,* 179: 751–756 (1994)).

For example, the functional assay of Sledziewski et al. using hybrid G protein coupled receptors can be used to monitor the ability a ligand or promoter to bind receptor and activate a G protein (Sledziewski et al., U.S. Pat. No. 5,284,746, the teachings of which are incorporated herein by reference).

A biological response of the host cell (triggered by binding to hybrid receptor) is monitored, detection of the response being indicative of the presence of ligand in the test sample. Sledziewski et al. describes a method of detecting the presence of a ligand in a test sample, wherein the ligand is a compound which is capable of being bound by the ligand-binding domain of a receptor. In one embodiment of the method, yeast host cells are transformed with a DNA construct capable of directing the expression of a biologically active hybrid G protein-coupled receptor (i.e., a fusion protein). The hybrid receptor comprises a mammalian G protein-coupled receptor having at least one domain other than the ligand-binding domain replaced with a corresponding domain of a yeast G protein-coupled receptor, such as a STE2 gene product. The yeast host cells containing the construct are maintained under conditions in which the hybrid receptor is expressed, and the cells are contacted with a test sample under conditions suitable to permit binding of ligand to the hybrid receptor. The assay is conducted as described and the biological response of the host cell (triggered by binding to hybrid receptor) is monitored, detection of the response being indicative of a signalling function.

For instance, an assay is provided In which binding to a hybrid receptor derived from STE2 gene product leads to induction of the BAR1 promoter. Induction of the promoter is measured by means of a reporter gene (β-gal), which is linked to the BAR1 promoter and introduced into host cells on a second construct. Expression of the reporter gene can be detected by an in vitro enzyme assay on cell lysates or by the presence of blue colonies on plates containing an indicator (X-gal) in the medium, for example.

Such assays can be preformed in the presence of the antibody to be assessed, and the ability of the antibody to inhibit the activity induced by the ligand or promoter is determined using known methods and/or methods described herein.

Chemotaxis and Assays of Cellular Stimulation

Chemotaxis assays can also be used to assess the ability of an antibody to block binding of a ligand to mammalian CCR5 and/or inhibit function associated with binding of the ligand to the receptor. These assays are based on the functional migration of cells in vitro or in vivo induced by a compound. The use of an in vitro transendothelial chemotaxis assay is described by Springer et al. (Springer et al., WO 94/20142, published Sep. 15, 1994, the teachings of which are incorporated herein by reference; see also Berman et al., *Immunol. Invest.* 17: 625–677 (1988)). Migration across endothelium into collagen gels has also been described (Kavanaugh et al., *J. Immunol.,* 146: 4149–4156 (1991)). Stable transfectants of mouse L1-2 pre-B cells or of other suitable host cells capable of chemotaxis can be used (see e.g., Example 1) in chemotaxis assays, for example.

Generally, chemotaxis assays monitor the directional movement or migration of a suitable cell (such as a leukocyte (e.g., lymphocyte, eosinophil, basophil)) into or through a barrier (e.g., endothelium, a filter), toward increased levels of a compound, from a first surface of the barrier toward an opposite second surface. Membranes or filters provide convenient barriers, such that the directional movement or migration of a suitable cell into or through a filter, toward increased levels of a compound, from a first surface of the filter toward an opposite second surface of the filter, is monitored. In some assays, the membrane is coated with a substance to facilitate adhesion, such as ICAM-1, fibronectin or collagen. Such assays provide an in vitro approximation of leukocyte "homing".

For example, one can detect or measure inhibition of the migration of cells in a suitable container (a containing means), from a first chamber into or through a microporous membrane into a second chamber which contains an antibody to be tested, and which is divided from the first chamber by the membrane. A suitable membrane, having a suitable pore size for monitoring specific migration in response to compound, including, for example, nitrocellulose, polycarbonate, is selected. For example, pore sizes of about 3–8 microns, and preferably about 5–8 microns can be used. Pore size can be uniform on a filter or within a range of suitable pore sizes.

To assess migration and inhibition of migration, the distance of migration into the filter, the number of cells crossing the filter that remain adherent to the second surface of the filter, and/or the number of cells that accumulate in the second chamber can be determined using standard techniques (e.g., microscopy). In one embodiment, the cells are labeled with a detectable label (e.g., radioisotope, fluorescent label, antigen or epitope label), and migration can be assessed in the presence and absence of the antibody by determining the presence of the label adherent to the membrane and/or present in the second chamber using an appropriate method (e.g., by detecting radioactivity, fluorescence, immunoassay). The extent of migration induced by an antibody agonist can be determined relative to a suitable control (e.g., compared to background migration determined in the absence of the antibody, compared to the extent of migration induced by a second compound (i.e., a standard), compared with migration of untransfected cells induced by the antibody).

Chambers can be formed from various solids, such as plastic, glass, polypropylene, polystyrene, etc. Membranes which are detachable from the chambers, such as a Biocoat (Collaborative Biomedical Products) or Transwell (Costar, Cambridge, Mass.) culture insert, facilitate counting adherent cells.

In the container, the filter is situated so as to be in contact with fluid containing cells in the first chamber, and the fluid in the second chamber. Other than the antibody (test compound) for the purpose of the assay, the fluid on either side of the membrane is preferably the same or substantially similar. The fluid in the chambers can comprise protein solutions (e.g., bovine serum albumin, fetal calf serum, human serum albumin) which may act to increase stability and inhibit nonspecific binding of cells, and/or culture media.

In a preferred embodiment, particularly for T cells, monocytes or cells expressing a mammalian CCR5, transendothelial migration is monitored. Such assays are better physiological models, because they more accurately recapitulate in vivo conditions in which leukocytes emigrate from blood vessels toward chemoattractants present in the tissues at sites of inflammation by crossing the endothelial cell layer lining the vessel wall. In addition, transendothelial assays have lower background and as a result a higher signal to noise ratio.

In this embodiment, transmigration through an endothelial cell layer is assessed. To prepare the cell layer, endothelial cells can be cultured on a microporous filter or membrane, optionally coated with a substance such as collagen, fibronectin, or other extracellular matrix proteins, to facilitate the attachment of endothelial cells. Preferably, endothelial cells are cultured until a confluent monolayer is formed. A variety of mammalian endothelial cells can are available for monolayer formation, including for example, vein, artery or microvascular endothelium, such as human umbilical vein endothelial cells (Clonetics Corp, San Diego, Calif.). To assay chemotaxis in response to a particular mammalian receptor, endothelial cells of the same mammal are preferred; however endothelial cells from a heterologous mammalian species or genus can also be used.

Generally, the assay is performed by detecting the directional migration of cells into or through a membrane or filter, in a direction toward increased levels of a compound, from a first surface of the filter toward an opposite second surface of the filter, wherein the filter contains an endothelial cell layer on a first surface. Directional migration occurs from the area adjacent to the first surface, into or through the membrane, towards a compound situated on the opposite side of the filter. The concentration of compound present in the area adjacent to the second surface, is greater than that in the area adjacent to the first surface.

In one embodiment used to test for an antibody inhibitor, a composition comprising cells capable of migration and expressing a mammalian CCR5 receptor can be placed in the first chamber. A composition comprising one or more ligands or promoters capable of inducing chemotaxis of the cells in the first chamber (having chemoattractant function) is placed in the second chamber. Preferably shortly before the cells are placed in the first chamber, or simultaneously with the cells, a composition comprising the antibody to be tested is placed, preferably, in the first chamber. Antibodies which can bind receptor and inhibit the induction of chemotaxis, by a ligand or promoter, of the cells expressing a mammalian CCR5 in this assay are inhibitors of receptor function (e.g., inhibitors of stimulatory function). A reduction in the extent of migration induced by the ligand or promoter in the presence of the antibody is indicative of inhibitory activity. Separate binding studies (see above) could be performed to determine whether inhibition is a result of binding of the antibody to receptor or occurs via a different mechanism.

In vivo assays which monitor leukocyte infiltration of a tissue, in response to injection of a compound (e.g., antibody) in the tissue, are described below (see Models of Inflammation). These models of in vivo homing measure the ability of cells to respond to a ligand or promoter by emigration and chemotaxis to a site of inflammation.

In addition to the methods described, the effects of an antibody on the stimulatory function of CCR5 can be assessed by monitoring cellular responses induced by active receptor, using suitable host cells containing receptor.

Identification of Additional Ligands, Inhibitors and/or Promoters of Mammalian CCR5 Function The assays described above, which can be used to assess binding and function of the antibodies of the present invention, can be adapted to identify additional ligands or other substances which bind a mammalian CCR5 protein, as well as inhibitors and/or promoters of mammalian CCR5 function. For example, agents having the same or a similar binding specificity as that of an antibody of the present invention or functional portion thereof can be identified by a competition assay with said antibody or portion thereof. Thus, the present invention also encompasses methods of identifying ligands of the receptor or other substances which bind a mammalian CCR5 protein, as well as inhibitors (e.g., antagonists) or promoters (e.g., agonists) of receptor function. In one embodiment, cells bearing a mammalian CCR5 protein or functional variant thereof (e.g., leukocytes or suitable host cells which have been engineered to express a mammalian CCR5 protein or functional variant encoded by a nucleic acid introduced into said cells) are used in an assay to identify and assess the efficacy of ligands or other substances which bind receptor, including inhibitors or promoters of receptor function. Such cells are also useful in assessing the function of the expressed receptor protein or polypeptide.

According to the present invention, ligands and other substances which bind receptor, inhibitors and promoters of receptor function can be identified in a suitable assay, and further assessed for therapeutic effect. Inhibitors of receptor function can be used to inhibit (reduce or prevent) receptor activity, and ligands and/or promoters can be used to induce (trigger or enhance) normal receptor function where indicated. Thus, the present invention provides a method of treating inflammatory diseases, including autoimmune disease and graft rejection, comprising administering an inhibitor of receptor function to an individual (e.g., a mammal). The present invention further provides a method of stimulating receptor function by administering a novel ligand or promoter of receptor function to an individual, providing a new approach to selective stimulation of leukocyte function, which is useful, for example, in the treatment of infectious diseases and cancer.

As used herein, a "ligand" of a mammalian CCR5 protein refers to a particular class of substances which bind to a mammalian CCR5 protein, including natural ligands and synthetic and/or recombinant forms of natural ligands, as well as infectious agents having a tropism for mammalian CCR5 positive cells (e.g., viruses such as HIV). A natural ligand of a selected mammalian receptor is of a mammalian origin which is the same as that of the mammalian CCR5 protein (e.g., a chemokine such as RANTES, MIP-1α, MIP-1β). In a preferred embodiment, ligand binding of a mammalian CCR5 protein occurs with high affinity.

As used herein, an "inhibitor" is a substance which inhibits (decreases or prevents) at least one function characteristic of a mammalian CCR5 protein (e.g., a human CXCR3), such as a binding activity (e.g., ligand binding, promoter binding), a signalling activity (e.g., activation of a mammalian G protein, induction of rapid and transient increase in the concentration of cytosolic free calcium $[Ca^{2-}]_i$), and/or cellular response function (e.g., stimulation of chemotaxis, exocytosis or inflammatory mediator release by leukocytes). An inhibitor is also a substance which inhibits HIV entry into a cell. The term inhibitor refers to substances including antagonists which bind receptor (e.g., an antibody, a mutant of a natural ligand, other competitive inhibitors of ligand binding), and substances which inhibit receptor function without binding thereto (e.g., an anti-idiotypic antibody).

As used herein, a "promoter" is a substance which promotes (induces, causes, enhances or increases) at least one function characteristic of a mammalian CCR5 protein (e.g., a human CCR5), such as a binding activity (e.g., ligand, inhibitor and/or promoter binding), a signalling activity (e.g., activation of a mammalian G protein, induction of rapid and transient increase in the concentration of cytosolic free calcium $[Ca^{2+}]_i$), and/or a cellular response function (e.g., stimulation of chemotaxis, exocytosis or inflammatory mediator release by leukocytes). The term promoter refers to substances including agonists which bind receptor (e.g., an antibody, a homolog of a natural ligand from another species), and substances which promote receptor function without binding thereto (e.g., by activating an associated protein). In a preferred embodiment, the agonist is other than a homolog of a natural ligand.

Thus, the invention also relates to a method of detecting or identifying an agent which binds a mammalian chemokine receptor 5 protein or ligand binding variant thereof, including ligands, inhibitors, promoters, and other substances which bind a mammalian CCR5 receptor or functional variant. According to the method, an agent to be tested, an antibody or antigen binding fragment of the present invention (e.g., 2D7, an antibody having an epitopic specificity which is the same as or similar to that of 2D7, and antigen binding fragments thereof) and a composition comprising a mammalian chemokine receptor 5 protein or a ligand binding variant thereof can be combined. The foregoing components are combined under conditions suitable for binding of the antibody or antigen binding fragment to mammalian chemokine receptor 5 protein or a ligand binding variant thereof, and binding of the antibody or fragment to the mammalian chemokine receptor 5 protein or ligand binding variant is detected or measured, either directly or indirectly, according to methods described herein or other suitable methods. A decrease in the amount of complex formed relative to a suitable control (e.g., in the absence of the agent to be tested) is indicative that the agent binds said receptor or variant. The composition comprising a mammalian chemokine receptor 5 protein or a ligand binding variant thereof can be a membrane fraction of a cell bearing recombinant chemokine receptor 5 protein or ligand binding variant thereof. The antibody or fragment thereof can be labeled with a label such as a radioisotope, spin label, antigen label, enzyme label, fluorescent group and chemiluminescent group.

In one embodiment, the invention relates to a method of detecting or identifying an agent which binds a mammalian chemokine receptor 5 protein or a ligand binding variant thereof, comprising combining an agent to be tested, an antibody or antigen binding fragment of the present invention (e.g., 2D7, an antibody having an epitopic specificity which is the same as or similar to that of 2D7, or antigen binding fragments thereof) and a cell bearing a mammalian chemokine receptor 5 protein or a ligand binding variant thereof. The foregoing components are combined under conditions suitable for binding of the antibody or antigen binding fragment to the CCR5 protein or ligand binding variant thereof, and binding of the antibody or fragment to the mammalian chemokine receptor 5 protein or variant is detected or measured, either directly or indirectly, by methods described herein and or other suitable methods. A decrease in the amount of complex formed relative to a suitable control is indicative that the agent binds the receptor or variant. The antibody or fragment thereof can be labeled with a label selected from the group consisting of a radioisotope, spin label, antigen label, enzyme label, fluorescent group and chemiluminescent group. These and similar assays can be used to detect agents, including ligands (e.g., chemokines or strains of HIV which interact with CCR5) or other substances, including inhibitors or promoters of receptor function, which can bind CCR5 and compete with the antibodies described herein for binding to the receptor.

The assays described above can be used, alone or in combination with each other or other suitable methods, to identify ligands or other substances which bind a mammalian CCR5 protein, and inhibitors or promoters of a mammalian CCR5 protein or variant. The in vitro methods of the present invention can be adapted for high-throughput screening in which large numbers of samples are processed (e.g., a 96-well format). Host cells expressing recombinant mammalian CCR5 (e.g., human CCR5) at levels suitable for high-throughput screening can be used, and thus, are particularly valuable in the identification and/or isolation of ligands or other substances which bind receptor, and inhibitors or promoters of mammalian CCR5 proteins. Expression of receptor can be monitored in a variety of ways. For instance, expression can be monitored using antibodies of the present invention which bind receptor or a portion thereof. Also, commercially available antibodies can be used to detect expression of an antigen- or epitope-tagged fusion protein comprising a receptor protein or polypeptide (e.g., FLAG tagged receptors), and cells expressing the desired level can be selected.

Nucleic acid encoding a mammalian CCR5 protein or functional variant thereof can be incorporated into an expression system to produce a receptor protein or polypeptide. An isolated and/or recombinant mammalian CCR5 protein or variant, such as a receptor expressed in cells stably or transiently transfected with a construct comprising a recombinant nucleic acid encoding a mammalian CCR5 protein or variant, or in a cell fraction containing receptor (e.g., a membrane fraction from transfected cells, liposomes incorporating receptor), can be used in tests for receptor function. The receptor can be further purified if desired. Testing of receptor function can be carried out in vitro or in vivo.

An isolated and/or recombinant mammalian CCR5 protein or functional variant thereof, such as a human CCR5, can be used in the present method, in which the effect of a compound is assessed by monitoring receptor function as described herein or using other suitable techniques. For example, stable or transient transfectants (e.g., baculovirus infected Sf9 cells, stable tranfectants of mouse L1.2 pre-B cells), can be used in binding assays. Stable transfectants of Jurkat cells or of other suitable cells capable of chemotaxis can be used (e.g., mouse L1.2 pre-B cells) in chemotaxis assays, for example.

According to the method of the present invention, compounds can be individually screened or one or more compounds can be tested simultaneously according to the methods herein. Where a mixture of compounds is tested, the compounds selected by the processes described can be separated (as appropriate) and identified by suitable methods (e.g., PCR, sequencing, chromatography). The presence of one or more compounds (e.g., a ligand, inhibitor, promoter) in a test sample can also be determined according to these methods.

Large combinatorial libraries of compounds (e.g., organic compounds, recombinant or synthetic peptides, "peptoids", nucleic acids) produced by combinatorial chemical synthesis or other methods can be tested (see e.g., Zuckerman, R. N. et al., *J. Med. Chem.*, 37: 2678–2685 (1994) and references cited therein; see also, Ohlmeyer, M. H. J. et al., *Proc. Natl. Acad. Sci. USA* 90:10922–10926 (1993) and DeWitt, S. H. et al., *Proc. Natl. Acad. Sci. USA* 90:6909–6913 (1993), relating to tagged compounds; Rutter, W. J. et al. U.S. Pat. No. 5,010,175; Huebner, V. D. et al., U.S. Pat. No. 5,182,366; and Geysen, H. M., U.S. Pat. No. 4,833,092). Where compounds selected from a combinatorial library by the present method carry unique tags, identification of individual compounds by chromatographic methods is possible.

In one embodiment, phage display methodology is used. For example, a mammalian CCR5 protein or functional variant, an antibody or functional portion thereof of the present invention, and a phage (e.g., a phage or collection of phage such as a library) displaying a polypeptide, can be combined under conditions appropriate for binding of the antibody or portion thereof to the mammalian CCR5 protein or variant (e.g., in a suitable binding buffer). Phage which can compete with the antibody or portion thereof and bind to the mammalian CCR5 protein or variant can be detected or selected using standard techniques or other suitable methods. Bound phage can be separated from receptor using a suitable elution buffer. For example, a change in the ionic strength or pH can lead to a release of phage. Alternatively, the elution buffer can comprise a release component or components designed to disrupt binding of compounds (e.g., one or more compounds which can disrupt binding of the displayed peptide to the receptor, such as a ligand, inhibitor, and/or promoter which competitively inhibits binding). Optionally, the selection process can be repeated or another selection step can be used to further enrich for phage which bind receptor. The displayed polypeptide can be characterized (e.g., by sequencing phage DNA). The polypeptides identified can be produced and further tested for binding, and for inhibitor or promoter function. Analogs of such peptides can be produced which will have increased stability or other desirable properties.

In one embodiment, phage expressing and displaying fusion proteins comprising a coat protein with an N-terminal peptide encoded by random sequence nucleic acids can be produced. Suitable host cells expressing a mammalian CCR5 protein or variant and an anti-CCR5 antibody or functional portion thereof, are combined with the phage, bound phage are selected, recovered and characterized. (See e.g., Doorbar, J. and G. Winter, *J. Mol. Biol.*, 244: 361 (1994) discussing a phage display procedure used with a G protein-coupled receptor).

Other sources of potential ligands or other substances which bind to, or inhibitors and/or promoters of, mammalian CCR5 proteins include, but are not limited to, variants of CCR5 ligands, including naturally occurring, synthetic or recombinant variants of MIP-1α, MIP-1β or RANTES, substances such as other chemoattractants or chemokines, variants thereof, other inhibitors and/or promoters (e.g., anti-CCR5 antibodies, antagonists, agonists), other G protein-coupled receptor ligands, inhibitors and/or promoters (e.g., antagonists or agonists), and soluble portions of a mammalian CCR5 receptor, such as a suitable receptor peptide or analog which can inhibit receptor function (see e.g., Murphy, R. B., WO 94/05695).

Models of Inflammation

In vivo models of inflammation are available which can be used to assess the effects of antibodies against CCR5 in vivo as therapeutic agents. For example, leukocyte infiltration upon intradermal injection of an antibody reactive with mammalian CCR5 into a suitable animal, such as rabbit, rat, or guinea pig, can be monitored (see e.g., Van Damme, J. et al., *J. Exp. Med.*, 176: 59–65 (1992); Zachariae, C. O. C. et al., *J. Exp. Med.* 171: 2177–2182 (1990); Jose, P. J. et al., *J. Exp. Med.* 179: 881–887 (1994)). In one embodiment, skin biopsies are assessed histologically for infiltration of leukocytes (e.g., eosinophils, granulocytes). In another embodiment, labeled cells (e.g., stably transfected cells expressing a mammalian CCR5, labeled with $^{111}$In for example) capable of chemotaxis and extravasation are administered to the animal. For example, an antibody to be assessed can be administered, either before, simultaneously with or after ligand or agonist is administered to the test animal. A decrease of the extent of infiltration in the presence of antibody as compared with the extent of infiltration in the absence of inhibitor is indicative of inhibition.

Diagnostic and Therapeutic Applications

The antibodies of the present invention are useful in a variety of applications, including research, diagnostic and therapeutic applications. In one embodiment, the antibodies are labeled with a suitable label (e.g., fluorescent label, chemiluminescent label, isotope label, epitope or enzyme label). For instance, they can be used to isolate and/or purify receptor or portions thereof, and to study receptor structure (e.g., conformation) and function.

In addition, the various antibodies of the present invention can be used to detect or measure the expression of receptor, for example, on T cells (e.g., CD8+ cells, CD45RO+ cells), monocytes and/or on cells transfected with a receptor gene. Thus, they also have utility in applications such as cell sorting (e.g., flow cytometry, fluorescence activated cell sorting), for diagnostic or research purposes.

Anti-idiotypic antibodies are also provided. Anti-idiotypic antibodies recognize antigenic determinants associated with the antigen-binding site of another antibody. Anti-idiotypic antibodies can be prepared a against second antibody by immunizing an animal of the same species, and preferably of the same strain, as the animal used to produce the second antibody. See e.g., U.S. Pat. No. 4,699,880.

In one embodiment, antibodies are raised against receptor or a portion thereof, and these antibodies are used in turn to produce an anti-idiotypic antibody. The anti-Id produced thereby can bind compounds which bind receptor, such as ligands, inhibitors or promoters of receptor function, and can be used in an immunoassay to detect or identify or quantitate such compounds. Such an anti-diotypic antibody can also be an inhibitor of mammalian CCR5 receptor function, although it does not bind receptor itself.

Anti-idiotypic (i.e., Anti-Id) antibody can itself be used to raise an anti-idiotypic antibody (i.e., Anti-anti-Id). Such an antibody can be similar or identical in specificity to the original immunizing antibody. In one embodiment, antibody antagonists which block binding to receptor can be used to raise Anti-Id, and the Anti-Id can be used to raise Anti-anti-Id, which can have a specificity which is similar or identical to that of the antibody antagonist. These anti-anti-Id antibodies can be assessed for their effects on receptor function.

Single chain, and chimeric, humanized or primatized (CDR-grafted), as well as chimeric or CDR-grafted single chain anti-idiotypic antibodies can be prepared, and are encompassed by the term anti-idiotypic antibody. Antibody fragments of such antibodies can also be prepared. mAb antagonists of CCR5 can be used as therapeutics for AIDS, as well as certain inflammatory diseases. HIV-1 and HIV-2 are the etiologic agents of acquired immunodeficiency syndrome (AIDS) in humans. AIDS results in part from the depletion of CD4+ T lymphocytes in HIV infected individuals. HIV-1 infects primarily T lymphocytes, monocytes/macrophages, dendritic cells and, in the central nervous system, microglia. All of these cells express the CD4 glycoprotein, which serves as a receptor for HIV-1 and HIV-2. Efficient entry of HIV into target cells is dependent upon binding of the viral exterior envelope glycoprotein, gp120, to the amino-terminal CD4 domain. After virus binding, the HIV-1 envelope glycoproteins mediate the fusion of viral and host cell membranes to complete the entry process. Membrane fusion directed by HIV-1 envelope glycoproteins expressed on the infected cell surface leads to cell-cell fusion, resulting in syncytia.

Recently, host cell factors in addition to CD4 have been suggested to determine the efficiency of HIV-1 envelope glycoprotein-mediated membrane fusion. The 7 transmembrane receptor (7TMR) termed HUMSTSR, LESTR, or "fusin" has been shown to allow a range of CD4-expressing cells to support infection and cell fusion mediated by laboratory-adapted HIV-1 envelope glycoproteins (Feng, Y., et al., *Science* (Wash. DC), 272:872–877 (1996)). Antibodies to HUMSTSR blocked cell fusion and infection by laboratory-adapted HIV-1 isolates but not by macrophage-tropic primary viruses in vitro (Feng, Y., et al., *Science* (Wash. DC), 272:872–877 (1996)).

It has been observed that infection of macrophage-tropic primary HIV-1 isolates, but not that of a laboratory-adapted isolate, could be inhibited by the β-chemokines RANTES, MIP-1α and MIP-1β (Cocchi, F., et al., *Science* (Wash. DC), 270:1811–1815 (1995)). High endogenous expression of these β-chemokines has also been suggested to account for the in vitro resistance to HIV-1 infection of CD4+ T cells from uninfected individuals with multiple sexual exposures to seropositive partners (Paxton, W. A., et al., *Nat. Med.,* 2:412–417 (1996)). This resistance was only seen for macrophage-tropic and not T cell line-tropic viruses and was influenced by the structure of the third variable (V3) gp120 region of the infecting virus. The available data suggested that at least one other host cell surface molecule besides CD4 and distinct from HUMSTSR facilitates the entry of primary, macrophage tropic HIV-1 isolates, and that this molecule might be influenced by interaction with β-chemokines.

The ability of chemokine receptors and related molecules to facilitate the infection of primary clinical HIV-1 isolates has been reported recently by five separate groups (see e.g., Bates, P., *Cell,* 86:1–3 (1996); Choe, H., et al., *Cell,* 85:1135–1148 (1996)). CCR5, when expressed along with CD4, allowed cell lines resistant to most primary HIV-1 isolates to be infected. Utilization of CCR5 on the target cell depended upon the sequence of the third variable (V3) region of the HIV-1 gp120 exterior envelope glycoprotein. These studies indicated that involvement of various members of the chemokine receptor family in the early stages of HIV-1 infection helps to explain viral tropism and β-chemokine inhibition of primary HIV-1 isolates. CCR5 is the principal co-receptor for primary macrophage-tropic HIV-1 strains (Choe et al., *Cell* 85:1135–1148 (1996); Alkhatib et al., *Science* 272:1955–1958 (1996); Doranz et al., *Cell* 85:1149–1158 (1996); Deng et al., *Nature* 381:661–666 (1996); Dragic et al., *Nature* 381:667–673 (1996)), while CXCR4 supports infection of CD4 cells by laboratory-adapted, T tropic HIV-1 strains (Feng et al., *Science* 272:872–877 (1996)). Recent studies have shown that the envelope glycoprotein gp120 of M-tropic HIV-1, upon binding to CD4, interacts specifically with the second co-receptor, CCR5 (Wu et al., *Nature* 384:179–183 (1996)).

There is evidence that at least some of the long term survivors of HIV-1 infection have defects in CCR5 expression. The significance of CCR5 for HIV-1 infection is suggested from recent studies involving long term survivors who have been multiply exposed to HIV-1 (Liu et al., *Cell* 86:367–377 (1996); Samson et al., *Nature* 382:722–725 (1996); Dean et al., *Science* 273:1856–1862 (1996); Huang et al., *Nature Med.* 2:1240–1243 (1996)). This resistance results from a defective CCR5 allele that contains an internal 32 base pair deletion (CCR5 Δ32). CCR5 Δ32 homozygous individuals comprise approximately 1% of the Caucasian population, and heterozygous individuals comprise approximately 15% (Liu et al., *Nature* 384:179–183 (1996); Samson et al., *Nature* 382:722–725 (1996); Dean et al., *Science* 273:1856–1862 (1996); Huang et al., *Nature Med.* 2:1240–1243 (1996)). To date, no immunological defects have been noted in either the CCR5 Δ32 homozygous individuals, or in heterozygous individuals. Moreover, CD4+T cells from these individuals were found to be highly resistant in vitro to the entry of primary macrophage-tropic virus (Liu et al., *Cell* 86:367–377 (1996); Paxton et al., *Nature Med.* 2:412–417 (1996)).

The present invention also provides a method of inhibiting HIV infection of a cell (e.g., new infection and/or syncytium formation) which expresses a mammalian CCR5 or portion thereof, comprising contacting the cell with an effective amount of an antibody or functional portion thereof which binds to a mammalian CCR5 or portion of said receptor.

Various methods can be used to assess binding of HIV to a cell and/or infection of a cell by HIV in the presence of the antibodies of the present invention. For example, assays which assess binding of gp120 or a portion thereof to the receptor, HIV infection and syncytium formation can be used (see, for example, Choe, H., et al., *Cell*, 85:1135–1148 (1996)). The ability of the antibody of the present invention to inhibit these processes can be assessed using these or other suitable methods.

In addition, the present invention provides a method of treating HIV in a patient, comprising administering to the patient an effective amount of an antibody or functional portion thereof which binds to a mammalian CCR5 or portion of said receptor. Therapeutic use of antibody to treat HIV includes prophylactic use (e.g., for treatment of a patient who may be or who may have been exposed to HIV). For example, health care providers who may be exposed or who have been exposed to HIV (e.g., by needle-stick) can be treated according to the method. Another example is the treatment of a patient exposed to virus after unprotected sexual contact or failure of protection.

In AIDS, multiple drug treatment appears the most promising. An anti-chemokine receptor antagonist that inhibits HIV infection can be added to the drug treatment regimen, in particular by blocking virus infection of new cells. Thus, administration of an antibody or fragment of the present administration in combination with one or more other therapeutic agents such as nucleoside analogues (e.g. AZT, 3TC, ddI) and /or protease inhibitors is envisioned, and provides an important addition to an HIV treatment regimen. In one embodiment, a humanized anti-CCR5 mAb is used in combination with a (i.e., one or more) therapeutic agent to reduce viral load from patients, by preventing fusion and/or infection of new cells. Such an antibody can also be useful in preventing perinatal infection.

The anti-CCR5 antibodies of the present invention also have value in diagnostic applications. An anti-CCR5 antibody can be used to monitor expression of this receptor in HIV infected individuals, similar to the way anti-CD4 has been used as a diagnostic indicator of disease stage. Expression of CCR5 has a correlation with disease progression, and can be used to identify low or high risk individuals for AIDS susceptibility.

For diagnostic purposes, the antibodies or antigen binding fragments can be labeled or unlabeled. Typically, diagnostic assays entail detecting the formation of a complex resulting from the binding of an antibody or fragment to CCR5. The antibodies or fragments can be directly labeled. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654 and 4,098,876). When unlabeled, the antibodies or fragments can be used in agglutination assays, for example. Unlabeled antibodies or fragments can also be used in combination with another (i.e., one or more) suitable reagent which can be used to detect antibody, such as a labeled antibody (e.g., a second antibody) reactive with the first antibody (e.g., anti-idiotype antibodies or other antibodies that are specific for the unlabeled immunoglobulin) or other suitable reagent (e.g., labeled protein A).

In one embodiment, the antibodies of the present invention can be utilized in enzyme immunoassays, wherein the subject antibodies, or second antibodies, are conjugated to an enzyme. When a biological sample comprising a mammalian CCR5 protein is combined with the subject antibodies, binding occurs between the antibodies and CCR5 protein. In one embodiment, a sample containing cells expressing a mammalian CCR5 protein, such as human blood, is combined with the subject antibodies, and binding occurs between the antibodies and cells bearing a human CCR5 protein comprising an epitope recognized by the antibody. These bound cells can be separated from unbound reagents and the presence of the antibody-enzyme conjugate specifically bound to the cells can be determined, for example, by contacting the sample with a substrate of the enzyme which produces a color or other detectable change when acted on by the enzyme. In another embodiment, the subject antibodies can be unlabeled, and a second, labeled antibody can be added which recognizes the subject antibody.

Kits for use in detecting the presence of a mammalian CCR5 protein in a biological sample can also be prepared. Such kits will include an antibody or functional portion thereof which binds to a mammalian chemokine receptor 5 protein or portion of said receptor, as well as one or more ancillary reagents suitable for detecting the presence of a complex between the antibody or fragment and CCR5 or portion thereof. The antibody compositions of the present invention can be provided in lyophilized form, either alone or in combination with additional antibodies specific for other epitopes. The antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the antibodies can be provided as a lyophilized mixture with the adjunct ingredients, or the adjunct ingredients can be separately provided for combination by the user. Generally these adjunct materials will be present in less than about 5% weight based on the amount of active antibody, and usually will be present in a total amount of at least about 0.001% weight based on antibody concentration. Where a second antibody capable of binding to the monoclonal antibody is employed, such antibody can be provided in the kit, for instance in a separate vial or container. The second antibody, if present, is typically labeled, and can be formulated in an analogous manner with the antibody formulations described above.

Similarly, the present invention also relates to a method of detecting and/or quantitating expression of a mammalian CCR5 or portion of the receptor by a cell, in which a composition comprising a cell or fraction thereof (e.g., membrane fraction) is contacted with an antibody or functional portion thereof (e.g., 5C7) which binds to a mammalian CCR5 or portion of the receptor under conditions appropriate for binding of the antibody thereto, and antibody binding is monitored. Detection of the antibody, indicative of the formation of a complex between antibody and CCR5 or a portion thereof, indicates the presence of the receptor. Binding of antibody to the cell can be determined as described above under the heading "Binding Assays", for example. The method can be used to detect expression of CCR5 on cells from an individual (e.g., in a sample, such as a body fluid, such as blood, saliva or other suitable sample). A quantitative expression of CCR5 on the surface of T cells or monocytes can be evaluated, for instance, by flow cytometry, and the staining intensity can be correlated with disease susceptibility, progression or risk.

The present invention also relates to a method of detecting the susceptibility of a mammal to infectious agent having a tropism for CCR5 positive cells (e.g., viruses such as HIV). That is, the method can be used to detect the susceptibility of a mammal to diseases which progress based on the amount of CCR5 present on cells and/or the number of CCR5 positive cells in a mammal. In one embodiment the invention relates to a method of detecting susceptibility of a mammal to HIV. In this embodiment, a sample to be tested is contacted with an antibody or functional portion thereof which binds to a mammalian CCR5 or portion thereof under conditions appropriate for binding of said antibody thereto, wherein the sample comprises cells which express CCR5 in normal individuals. The binding of antibody and/or amount of binding is detected, which indicates the susceptibility of the mammal to HIV, wherein higher levels of receptor correlate with increased susceptibility of the mammal to HIV. Thus, the method can be used to determine the expression level of CCR5 on the T cells of a susceptible but uninfected individual to determine the degree of risk to such an individual upon exposure to HIV. As discussed above, expression of CCR5 has a correlation with HIV disease progression. The antibodies of the present invention can also be used to further elucidate the correlation of CCR5 expression or of particular allelic forms of CCR5 with HIV disease progression in a mammal.

The present invention also encompasses a method of determining the prognosis for HIV in a mammal. According to the method, a sample to be tested is contacted with an antibody or functional portion thereof which binds to a mammalian CCR5 or portion thereof under conditions appropriate for binding of said antibody thereto, wherein the sample comprises cells which express CCR5 in normal individuals. The binding of antibody and/or amount of binding is detected, which indicates the prognosis for HIV in the mammal, wherein higher levels correlate with a poorer prognosis. Thus, the method can be used to monitor the course of HIV infection in a patient (e.g., by monitoring reduction of CCR5+, CD4+ cells over time). For example, the method can be used to estimate the appearance of full blown AIDS in a patient and/or determine the timing for appropriate treatment based on the disease progression.

Another aspect of the invention relates to a method of preventing HIV infection in an individual, comprising administering to the individual an effective amount of an antibody or functional portion thereof which binds to CCR5. According to the method, preventing HIV infection includes treatment in order to prevent (reduce or eliminate) infection of new cells in an infected individual or in order to prevent infection in an individual who may be, may have been, or has been, exposed to HIV. For example, individuals such as an HIV infected individual, a fetus of an HIV infected female, or a health care worker may be treated according to the method of the present invention.

Apart from their new found role in HIV infection, chemokine receptors function in the migration of leukocytes throughout the body, particularly to inflammatory sites. Inflammatory cell emigration from the vasculature is regulated by a three-step process involving interactions of leukocyte and endothelial cell adhesion proteins and cell specific chemoattractants and activating factors (Springer, T. A., *Cell*, 76:301–314 (1994); Butcher, E. C., *Cell*, 67:1033–1036 (1991); Butcher, E. C. and Picker, L. J., *Science (Wash. D.C.)*, 272:60–66 (1996)). These are: (a) a low affinity interaction between leukocyte selectins and endothelial cell carbohydrates; (b) a high-affinity interaction between leukocyte chemoattractant receptors and chemoattractant/activating factors; and (c) a tight-binding between leukocyte integrins and endothelial cell adhesion proteins of the immunoglobulin superfamily. Different leukocyte subsets express different repertoires of selections, chemoattractant receptors and integrins. Additionally, inflammation alters the expression of endothelial adhesion proteins and the expression of chemoattractant and leukocyte activating factors. As a consequence, there is a great deal of diversity for regulating the selectivity of leukocyte recruitment to extravascular sites. The second step is crucial in that the activation of the leukocyte chemoattractant receptors is thought to cause the transition from the selectin-mediated cell rolling to the integrin-mediated tight binding. This results in the leukocyte being ready to transmigrate to perivascular sites. The chemoattractant/chemoattractant receptor interaction is also crucial for transendothelial migration and localization within a tissue (Campbell, J. J., et al., *J. Cell Blol.*, 134:255–266 (1996); Carr, M. W., et al., *Immunity*, 4:179–187 (1996)). This migration is directed by a concentration gradient of chemoattractant leading towards the inflammatory focus.

The importance of chemokines in leukocyte trafficking has been demonstrated in several animal models. For example, neutralizing antibodies to IL-8 inhibit neutrophil recruitment to sites of inflammation such as in endotoxin-induced pleurisy and reperfusion injury (Broaddus, V. C., et al., *J. Immunol.*, 152:2960–2967 (1994); Mulligan, M. S., et al., *J. Immunol.*, 150:5585–5595 (1993); Sekido, N., et al., *Nature* (Lond.), 365:654–657 (1993)). Neutrophil recruitment is also impaired in IL-8 receptor knockout mice (Cacalano, G., et al., *Science* (Wash., D.C.), 265:682–684 (1994)). MIP-1α knockout mice were shown to have reduced inflammatory responses to viral infection (Cook, D. N., et al., *Science* (Wash., D.C.), 269:1583–1585 (1995)) as demonstrated by a delay in T cell dependent viral clearance of influenza, and elimination of coxsackie virus mediated myocarditis. Furthermore, neutralizing antibodies to MIP-1α were reported to influence eosinophil recruitment into mouse lung in a model of antigen-specific airway inflammation (Lukacs, N. W., et al., *Eur. J. Immunol.*, 25:245–251 (1995)). Finally, antibodies to MCP-1 were able to block monocyte recruitment in a granuloma model (Flory, C. M., et al., *Lab. Invest.*, 69:396–404 (1993)) and to completely inhibit T cell recruitment and cutaneous delayed-type hypersensitivity-induced inflammation in rats (Rand, M. L., et al., *Am. J. Path.*, 148:855–864 (1995)).

CCR5 has an important role in leukocyte trafficking, apart from its role in HIV infection. It is likely that CCR5 is a key chemokine receptor for T cell or T cell subset migration to certain inflammatory sites, and so anti-CCR5 mAbs can be used to inhibit (reduce or prevent) T cell migration, particularly that associated with T cell dysfunction, such as autoimmune disease, or allergic reactions. Accordingly, the antibodies of the present invention can also be used to modulate receptor function in research and therapeutic applications. For instance, the antibodies described herein can act as inhibitors to inhibit (reduce or prevent) (a) binding (e.g., of a ligand, an inhibitor or a promoter) to the receptor, (b) a receptor signalling function, and/or (c) a stimulatory function. Antibodies which act as inhibitors of receptor function can block ligand or promoter binding directly or indirectly (e.g., by causing a conformational change). For example, antibodies can inhibit receptor function by inhibiting binding of a ligand, or by desensitization (with or without inhibition of binding of a ligand). Antibodies which bind receptor can also act as agonists of receptor function, triggering or stimulating a receptor function, such as a signalling and/or a stimulatory function of a receptor (e.g., leukocyte trafficking) upon binding to receptor.

Thus, the present invention provides a method of inhibiting leukocyte trafficking in a mammal (e.g., a human patient), comprising administering to the mammal an effective amount of an antibody or functional portion thereof which binds to a mammalian CCR5 or portion of said receptor. Diseases which can be treated according to the method include autoimmune diseases such as multiple sclerosis, arthritis, and psoriasis, as well as allergic diseases, such as asthma. Administration of an antibody which binds CCR5 can result in amelioration or elimination of the disease state.

The antibody of the present invention, or a functional portion thereof, can also be used to treat disorders in which activation of the CCR5 receptor by binding of chemokines is implicated. For example, the antibodies or functional portions thereof (e.g., 2D7) can be used to treat allergy, atherogenesis, anaphylaxis, malignancy, chronic and acute inflammation, histamine and IgE-mediated allergic reactions, shock and rheumatoid arthritis.

Diseases or conditions of humans or other species which can be treated with inhibitors of CCR5 receptor function (including antibodies or portions thereof), include, but are not limited to:

inflammatory or allergic diseases and conditions, including respiratory allergic diseases such as asthma, allergic rhinitis, hypersensitivity lung diseases, hypersensitivity pneumonitis, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; inflammatory bowel diseases, such as Crohn's disease and ulcerative colitis; spondyloarthropathies; scleroderma; psoriasis and inflammatory dermatoses such as dermatitis, eczema, atopic dermatitis, allergic contact dermatitis, urticaria; vasculitis (e.g., necrotizing, cutaneous, and hypersensitivity vasculitis);

autoimmune diseases, such as arthritis (e.g., rheumatoid arthritis, psoriatic arthritis), multiple sclerosis, systemic lupus erythematosus, myasthenia gravis, juvenile onset diabetes, nephritides such as glomerulonephritis, autoimmune thyroiditis, Behcet's disease;

graft rejection (e.g., in transplantation), including allograft rejection or graft-versus-host disease;

cancers with leukocyte infiltration of the skin or organs; other diseases or conditions (including CCR5-mediated diseases or conditions), in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with promoters of CCR5 receptor function (including antibodies or portions thereof), include, but are not limited to:

immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; and immunosuppression due congenital deficiency in receptor function or other causes. Anti-CCR5 antibodies of the present invention can block the binding of one or more chemokines, thereby blocking the downstream cascade of one or more events leading to the above disorders.

Modes of Administration

According to the method, one or more antibodies can be administered to the host by an appropriate route, either alone or in combination with (before, simultaneously with, or after) another drug. For example, the antibodies of the present invention can also be used in combination with other monoclonal or polyclonal antibodies or with existing blood plasma products, such as commercially available gamma globulin and immune globulin products used in prophylactic or therapeutic treatments. The antibodies of the present invention can be used as separately administered compositions given in conjunction with antibiotics and/or antimicrobial agents.

An effective amount of an antibody (i.e., one or more antibodies or fragments) is administered. An effective amount is an amount sufficient to achieve the desired therapeutic effect, under the conditions of administration, such as an amount sufficient for inhibition of a CCR5 function, and thereby, inhibition of an inflammatory response or HIV infection, or an amount sufficient for promotion of a CCR5 function.

A variety of routes of administration are possible including, but not necessarily limited to, oral, dietary, topical, parenteral (e.g., intravenous, intraarterial, intramuscular, subcutaneous injection), inhalation (e.g., intrabronchial, intranasal or oral inhalation, intranasal drops), depending on the disease or condition to be treated. Other suitable methods of administration can also include rechargeable or biodegradable devices and slow release polymeric devices. The pharmaceutical compositions of this invention can also be administered as part of a combinatorial therapy with other agents.

Formulation of an antibody or fragment to be administered will vary according to the route of administration selected (e.g., solution, emulsion, capsule). An appropriate pharmaceutical composition comprising an antibody or functional portion thereof to be administered can be prepared in a physiologically acceptable vehicle or carrier. A mixture of antibodies and/or fragments can also be used. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. A variety of appropriate aqueous carriers are known to the skilled artisan, including water, buffered water, buffered saline, polyols (e.g., glycerol, propylene glycol, liquid polyethylene glycol), dextrose solution and glycine. intravenous vehicles can include various additives, preservatives, or fluid, nutrient or electrolyte replenishers (See, generally, *Remington's Pharmaceutical Science,* 16th Edition, Mack, Ed. 1980). The compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate. The antibodies of this invention can be lyophilized for storage and reconstituted in a suitable carrier prior to use according to art-known lyophilization and reconstitution techniques. The optimum concentration of the active ingredient(s) in the chosen medium can be determined empirically, according to procedures well known to the skilled artisan, and will depend on the ultimate pharmaceutical formulation desired. For inhalation, the compound can be solubilized and loaded into a suitable dispenser for administration (e.g., an atomizer, nebulizer or pressurized aerosol dispenser).

EXAMPLES

The present invention will now be illustrated by the following Examples, which are not intended to be limiting in any way. The teachings of all references cited herein are incorporated herein by reference.

Example 1

Generation and Identification of mAb to CCR5

Cells, Cell Lines, and Tissue Culture

Eosinophils were isolated from heparinized blood using CD 16 microbeads (Miltenyi Biotec, Auburn, Calif.), as described in Ponath, P. D., et al., *J. Clin. Invest.,* 97:604–612 (1996) and were shown cytologically to be ≧99% pure. Neutrophils and PBMCs were isolated as described in Ponath, P. D., et al., *J. Clin. Invest.,* 97:604–612 (1996). To generate CD3 blasts, $2\times10^6$ PBMC/ml in RPMI-1640 plus 10% FCS were added to tissue culture plates first coated with the anti-CD3 antibody TR66. After 4–6 days blasts were removed to fresh media and supplemented with IL-2 (provided by Antonio Lanzavecchia, Basel) at 50 units/ml. Other cell lines used included transfectants of the L1.2 murine pre B cell lymphoma, expressing high levels of either CCR3 (Ponath, P. D., et al., *J. Exp. Med.,* 183:2437–2448 (1996)), IL-8 RA (CXCR1) (Ponath, P. D., et al., *J. Exp. Med.,* 183:2437–2448 (1996)), IL-8 RB (CXCR2) (Ponath, P. D., et al., *J. Exp. Med.,* 183:2437–2448 (1996)), CCR2b, CCR4 and CCR5, and CCR1 (Campbell, J. J., et al., *J. Cell Biol.,* 134:255–266 (1996)). Transfectants were maintained in RPMI-1640 supplemented with 10% bovine serum and 800 μg/ml G418 or mycophenolic acid. The different transfectants were monitored for expression of the relevant receptors, using mAbs specific for CCR3 (Ponath, P. D., et al., *J. Exp. Med.,* 183:2437–2448 (1996)), IL-8 RA, IL-8 RB, or CCR2 (Qin, S., et al., *Eur. J. Immunol.* 26:640–647 (1996); (Ponath, P. D., et al., *J. Clin. Invest.,* 97:604–612 (1996)).

The CCR5 transfectant cells were maintained in selective medium. When needed, they were grown in non-selective medium for at least 24 hours before the experiment, and receptor expression was not lost when kept in non-selective medium for up to 1 week.

Expression Vector Construction and Generation of CCR5 Stable Transfectants

CCR5 cDNA (Raport, C. J., *J. Biol. Chem.,* 271:17161–17166 (1996)) was obtained by RT-PCR using a 5'-oligonucleotide primer 5' (CCCCTCGAGATGGACTACAAGGACGACGATGAC AAGGATTATCAAGTGTCAAGTCC) (SEQ ID NO:3) and 3'-oligonucleotide primer 5' (CCCTCTAGATTACAAGCCCACAGATATTTCCTGC TCCCC (SEQ ID NO:4) which contained flanking XhoI and XbaI sites, respectively. The 5' primer also contained a Flag epitope (Asp.Tyr.Lys.Asp.Asp.Asp.Asp.Lys) (SEQ ID NO:7). The template for the RT-PCR was total RNA made from KG1a cells (ATCC). The reaction conditions used were described in the Perkin-Elmer RT-PCR kit.

The PCR fragment was subcloned into the XhoI-XbaI sites of pCDNA3 (Invitrogen) and this construct was designated CCR5/pCDNA3 (NR54). Another expression vector, CCR5/pMRB101, was constructed in which the 1.1 kb CCR5 cDNA insert of CCR5/pCDNA3 construct was subcloned into the HindIII-XbaI sites of pMRB101 (Martin Robinson, CellTech). PCR fragments were sequenced to ascertain the sequence fidelity. In both of these expression vectors, the expression of the inserted gene was driven by a CMV promoter. The DNA was stably transfected into a murine pre-3 lymphoma cell line (L1.2) as described (Ponath, P. D., et al., *J. Exp. Med.,* 183:2437–2448 (1996)), except that with the CCR5/pMRB101 construct, the mycophenolic acid-selective medium was used to select for transfectants. The cell surface expression of CCR5 was monitored by staining with anti-FLAG mAb, and cells with high level expression were enriched by several rounds of limiting dilution and rescreening. For monoclonal antibody production, the L1.2 cell line transfected with CCR5/pMRB101 (NR56), treated with 5 mM butyric acid for 16–18 hours, was used exclusively for immunizing mice.

The murine pre-B lymphoma cell line L1.2 was maintained in RPMI-1640 supplemented with 10% bovine serum. 20 μg of the FLAG-tagged CCR-5/pMRB101 construct were linearized by digestion with SalI and used to transfect the L1.2 cell line as follows. L1.2 cells were washed twice in HBSS and resuspended in 0.8 ml of the same buffer. The plasmid DNA was mixed with the cells and incubated for 10 minutes at room temperature, transferred to a 0.4-cm electroporation cuvette, and a single pulse was applied at 250 V, 960 μF. The electroporation was followed by a 10 minute incubation at room temperature. Cells were changed to selective medium, as described above, 48 hours after transfection and the cells were plated in 96-well plates at 25,000 cells/well. After 2–3 weeks under drug selection, mycophenolic acid-resistant cells were stained with M2 monoclonal antibody, and analyzed by FACScan® (Becton Dickinson & Co., Mountain View, Calif.). For mAb staining, cells were washed once with PBS, and resuspended in 100 μl PBS containing 2% FCS, 0.1 sodium azide (FACS® buffer), 5 μg/ml affinity purified antibody or 5 μg/ml MOPC-21 IgG$_1$-isotype matched control mAb (Sigma Chemical Co., St. Louis, Mo.), or 100 μL hybridoma culture supernatant. After 30 minutes at 4° C., cells were washed twice with FACS® buffer, and resuspended in 100 μl FITC-conjugated, affinity-purified F(ab')$_2$ goat anti-mouse IgG (Jackson ImmunoResearch Laboratories). After incubation for 30 minutes at 4° C., cells were washed twice in FACS® buffer and analyzed by FACScan®. Propidium iodide was used to exclude dead cells. In some experiments, stable transfectants were treated with 5 mM n-butyric acid (Sigma Chemical Co., St. Louis, Mo., Catalog No. B 5887) 16–18 hours prior to analysis (FACS staining or binding) or immunization. Lines with detectable surface staining were expanded and cloned several times by limiting dilution. In addition, ligand binding was used to assess the level of expression. A CCR5 transfected clone having the highest number of binding sites per cell (Bmax=60,000–80,000 binding sites/cell) was used as immunogen as described below.

Chemotaxis of CCR5 L1.2 Transfectants

The Biocoat transwell tissue culture inserts (Collaborative Biomedical Products, MA) were used for the chemotaxis assays. The cells were incubated for 5–6 hours at 37° C. and the number of cells migrated to the lower chamber were counted on the FACS using forward and side scatter. In these studies, 10 nM of each chemokine was used.

Selection of Transfectants

To produce mAbs to CCR5, murine pre-B lymphoma L1.2 cells, expressing high levels of CCR5 were selected and maintained over several months. Cell lines expressing high levels have been generated, as described above, however these were continually monitored to ensure that receptor expression did not drift downward. Ligand binding and Scatchard analysis were performed routinely to ascertain receptor level on the transfectants, using radiolabeled MIP-1β, MIP-1α and RANTES. Routine chemotaxis assays were also performed to ensure that the lines responded correctly in a functional assay. To produce lines that express higher levels of the receptor, the L1.2 cells were cloned by limiting dilution in 96 well plates, or FACs sorted using a FACS advantage. Clones that grew up were assessed for receptor expression, using the anti-FLAG mAb and flow cytometry. Ligand binding was also used to assess the level of receptor expression.

Ligand Binding $^{125}$I-labeled human MIP-1α and MIP-1β were purchased from DuPont NEN (Boston, Mass.), and cold chemokines were from Peprotech (Rocky Hill, N.J.). CCR5/L1.2 cells were washed and resuspended in binding buffer (50 mM HEPES, pH 7.5, 1 mM $CaCl_2$, 5 mM $MgCl_2$, and 0.5% BSA) at $5 \times 10^6$ cells/ml. For each binding reaction (in a final volume of 100 µl), 25 µl cell suspension ($1.25 \times 10^5$ cells) was mixed with 0.1 nM radio-labeled chemokine with or without appropriate amount of anti-CCR5 mAb. Total binding was in the presence of radio-labeled chemokines only, and non-specific binding (background) was determined in the presence of 100 nM cold chemokines. The reactions were incubated at 37° C. for 30–45 minutes, and stopped by transferring the mixture to GFB filter plates which were then washed 2–3 times with binding buffer containing 0.5 M NaCl. The plates were dried and MicroScint scintillation fluid was added before counting. Each sample was done with at least duplicates.

Monoclonal Antibody Production and Flow Cytometry

L1.2 cells transfected with CCR5/pMRB101, prepared as described above, were washed three times in PBS and resuspended in 200 µl PBS/$10^7$ cells. Monoclonal antibodies reactive with CCR5 were generated by immunizing C57BL6 mice with $10^7$ L1.2 CCR5 transfected cells, intraperitoneally, six times at 2 week intervals. The final immunization was injected intravenously. Three days later, the spleen was removed and cells were fused with the SP2/0 cell line as described (Coligan, J. E. et al., 1992, In: *Current Protocols In Immunology* (John Wiley and Sons, New York), Unit 2.5.4).

Monoclonal antibodies reactive with CCR5 were identified using untransfected and L1.2 cells transfected with CCR5/pMRB101, and immunofluorescent staining analysis using a FACScan® (Becton Dickinison & Co., Mountain View, Calif.). Hybridoma culture supernatants were used in an indirect immunofluorescence assay in a 96-well format using anti-mouse Ig-FITC. Jntransfected and CCR5 transfected L1.2 cells were washed once with PBS, and resuspended in 50 µl PBS containing 2% FCS, 0.1% sodium azide (FACS® buffer). 50 µL hybridoma culture supernatant was added. After 30 minutes at 4° C., cells were washed twice with FACS® buffer, and resuspended in 100 µl FITC-conjugated, affinity-purified $F(ab')_2$ goat anti-mouse IgG (Jackson ImmunoResearch Laboratories). After incubation for 30 minutes at 4° C., cells were washed twice in FACS® buffer and analyzed by FACScan®. Antibodies which stained CCR5 transfectants, but not untransfected L1.2 cells, were selected.

Results

CCR5 was expressed in L1.2 cells, by stably transfecting a CCR5/pcDNA3 or CCR5/pMRB101 expression construct tagged with an eight amino acid residue epitope, FLAG. Stable transfectants were selected by their ability to stain with the anti-FLAG mAb, M2, and high expressors were enriched by limiting dilution cloning, and FACS analysis. Ligand binding and Scatchard analysis showed that the CCR5 transfectants bound MIP-1α, MIP-1β, and RANTES with high affinity (Kd=0.2–0.9 nM), and the receptor was expressed at a high level (Bmax=60,000–80,000 binding sites/cell). IL-8 and MCP-1 did not show any specific binding to these transfectants, nor could they compete the binding of $^{125}$I-MIP-1α, $^{125}$I-MIP-1β, or $^{125}$I-PANTES. It was found that the treatment of these cells with 5 mM butyrate could enhance the expression of CCR5 by 2–3 fold, i.e., a receptor level of ~200,000 sites per cell. The ability of the CCR5 transfectants to chemotax in response to various chemokines was also examined. CCR5/L1.2 transfectants chemotaxed very well to MIP-1α, MIP-1β, and RANTES, but had no detectable response to IL-8 or MCP-1.

A murine monoclonal antibody specific for human CCR5, designated 5C7, was produced as described herein. mAbs reactive with CCR5 were generated by immunizing mice with L1.2 cells transfected with CCR5/pMRB101, which expressed high levels of CCR5. Ten female C57BL6 mice were immunized with $10^7$ cells, intra-peritoneally, six times at 2 wk intervals, and a total of 6 fusions were performed, to identify a CCR5 specific mAb. In one fusion, 12 mAbs were identified that reacted with L1.2 cells expressing CCR5. The typical FACScan® profile of one of these mAbs, 5C7, is shown in FIG. 1. This mAb stained L1.2 CCR5 transfectants (solid profile), but not L1.2 cells transfected with other 7TMS receptors, such as CCR1, CXCR1, CXCR2, CXCR3, or wild type L1.2 cells (broken profiles). Negative control staining of all the transfectants with an irrelevant mAb yielded profiles similar to those shown for 5C7 staining on CCR1, CXCR1, CXCR2 or CXCR3. Anti-CCR5 mAbs were also found to stain a subset of human T cells from most donors (FIGS. 2A–2C), but were unreactive with neutrophils and eosinophils. Blood monocytes were weakly stained by mAb 5C7.

The 5C7 hybridoma cell line was deposited on Oct. 25, 1996 on behalf of LeukoSite, Inc., under the terms of the Budapest Treaty at the American Type Culture Collection, 10801 University Boulevard, Manassas, Va. 20110-2209 under Accession Number HB-12222.

Example 2

Expression of CCR5 on T Cells, and Correlation with Presence of the CCR5 Deletion Allele Genomic DNA was isolated from PBMC of selected blood donors using Trizol reagent according to the manufacturer's instructions (GibcoBRL). Upstream and downstream oligonucleotide primers for amplifying the CCR5 gene correspond to the second extracellular region of CCR5, and their sequences were as follows:

5'-primer, 5'-GAAGTTCCTCATTACACCTGCAGCTCTC (SEQ ID NO:5);

3'-primer,
5'-CTTCTTCTCATTTCGACACCGAAGCAGAG (SEQ ID NO:6).
Using this set of primers, the wild-type CCR5 allele will give rise to a PCR fragment of 174 bp, whereas the PCR fragment amplified from the deleted allele will be 142 bp. For each PCR reaction (100 μl volume), 1 μg genomic DNA was first denatured at 95° C. for 5 min., and amplified by 5 cycles of PCR (94° C., 45 s; 55° C., 45 s; 72° C., 45 s) followed by an additional 35 cycles (94° C., 45 s; 62° C., 45 s; 72° C., 30 s). The reaction products (25 μl) were run on a 4% Nusieve GTG agarose gel and DNA bands stained by ethidium bromide.

Results

To confirm that the mAbs were specific for CCR5, and to assess the usefulness of the mAbs for determining expression levels of CCR5 on T cells, PBMC from a large number of donors were assessed for CCR5 expression, using the mAb 5C7. The staining of PBMC from 50 blood donors revealed three staining patterns on lymphocytes. Several donors' PBMC were completely unreactive with mAb 5C7, typified by Donor 1 in FIG. 2C, whereas the majority of donors' PBMC showed a staining pattern in which approximately 10–20% of lymphocytes were intensely stained, typified by Donor 5 in FIG. 2A. Eight donors' PBMC showed a weak staining of a smaller percentage of lymphocytes, usually <5% (see Donor 3 in FIG. 2B). Recently, a mutant form of the CCR5 gene, containing a 32 base pair deletion (Δ32) which renders the molecule inactive and incapable of cell surface expression, has been identified (Dean, et al., Science, 273:1856 (1996); Liu, et al., Cell, 86:367–377 (1996)). Individuals homozygous for this mutant form of CCR5 were shown to be resistant to infection with HIV-1, indicating that the CCR5 receptor was a critical element for HIV transmission (Dean, et al., Science, 273:1856 (1996); Liu, et al., Cell, 86:367–377 (1996)). In addition, individuals with one normal and one mutant copy of the CCR5 gene (heterozygous individuals) also showed evidence of increased survival following HIV-1 infection (Dean, et al., Science, 273:1856 (1996)). Blood donors were assessed for the presence of the CCR5 deletion allele, using PCR primers, designed to distinguish a 174 base pair PCR product for normal CCR5, and a 142 bp product for the mutant form of CCR5. Heterozygous individuals show both the 174 and 142 bp products. FIG. 3A shows the position of the CCR5 deletion, and the sequence difference between the normal form of CCR5 (CCR5 wild type (WT), SEQ ID NO:1) and mutant form of CCR5 (CCR5 MUT, SEQ ID NO:2).

Figure 3B:
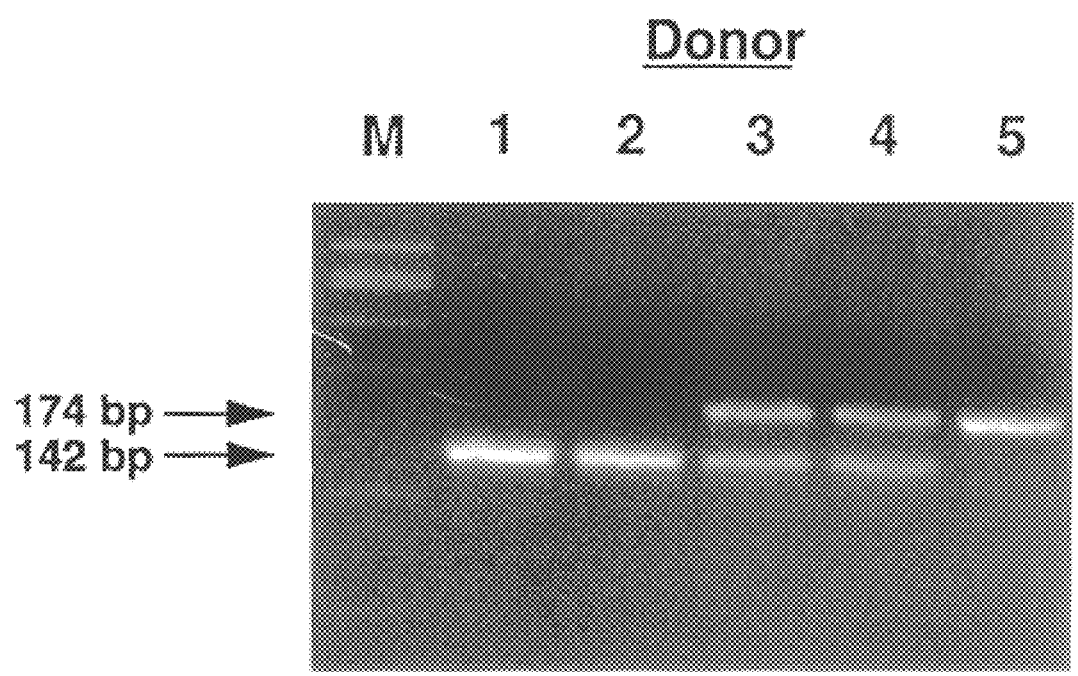

FIG. 3B shows an agarose gel with the PCR products amplified from the DNA of selected individuals. The positions of the 174 and 142 bp products are indicated by arrows. Donors 1 and 2 contained only the 142 bp product, indicating that these individuals were homozygous for the CCR5 mutant allele. Donors 3 and 4 contained both the 174 and 142 bp product indicating that they were heterozygous, containing one CCR5 mutant allele, and one normal CCR5 allele. Donor 5 showed only the 174 bp product, indicating that this individual had two normal copies of the CCR5 gene. Markers (Lane M) were run in order to determine the size of the various DNA products.

Example 3
Identity of CCR5-Positive Lymphocytes in Human Blood

Figure 5B:
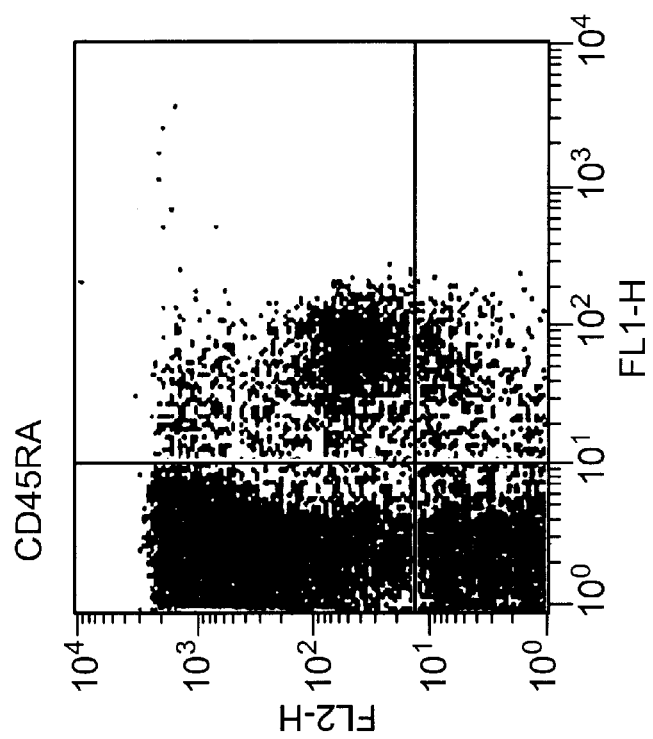
Figure 5A:
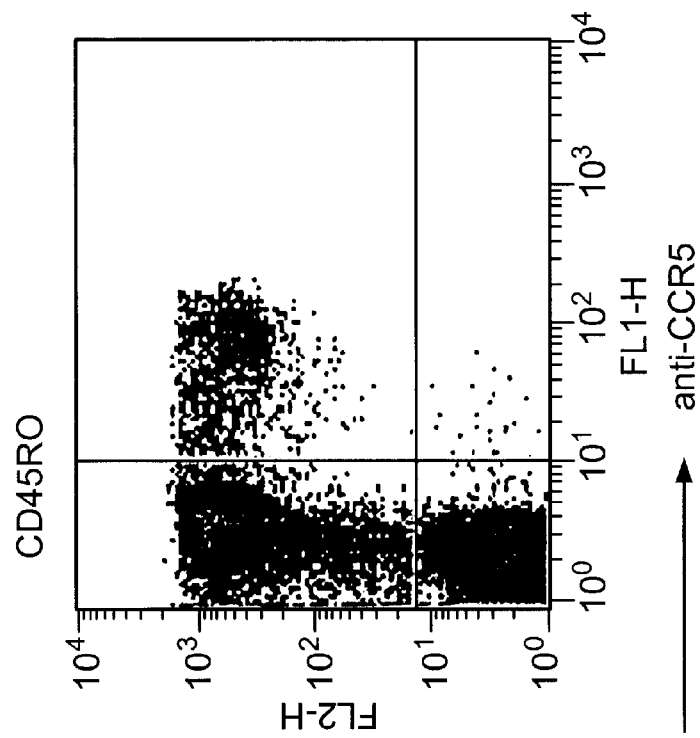

The expression of CCR5 on human lymphocytes was assessed, to determine which subset expressed CCR5 and CD4, and therefore might be most susceptible to infection by HIV-1. A two color immunofluorescence analysis was performed, using a variety of reagents recognizing human leukocyte surface molecules, such as CD45RO, CD45RA, CD26, CD25, CD4, and CD8. The level of control staining was determined using a variety of non-specific reagents, and quadrants were set for each plot based on this staining. FIGS. 4A–4B show that CCR5 was expressed on CD4+ T cells (FIG. 4A), as well as on CD8+ T cells (FIG. 4B), although CCR5 was expressed preferentially on the CD8+ subset. These cells expressed high levels of CD45RO, indicative of a memory phenotype, but also expressed low levels of the CD45RA molecule (FIGS. 5A–5B). CD26 has been used as a marker of acute activation of T cells, and the CCR5 positive cells were found to be CD26-hi or intermediate (FIG. 5C). CCR5 was largely absent from the IL-2 receptor (CD25+) subset (FIG. 5D).

Example 4
Generation and Identification of Additional mAb to CCR5 and Assessment of Chemokine and HIV-1 gp120 Binding
CCR5/CCR2 Chimeras A variety of CCR5/CCR2 chimeras (C25-01 to C25-14) were constructed by transferring restriction fragments flanked by the common BamHI, AflII, ClaI, EcoRI, and XbaI sites between human CCR5 and human CCR2b. The construction and characterization of these chimeras has been described previously (Rucker et al., Cell, 87:437–446 (1996)). The constructs were transferred into a bicistronic vector (Ghattas et al., Mol. Cell. Biol. 11:5848 (1991)), under control of the elongation factor 1α (EF1α) promoter, and transfected in CHO-k1 cells as described by Perret et al. (Biochem. Biophys. Res. Commun. 17:1044 (1990)). G418-resistant cell populations were used in FACS analyses.

Cells and Cell Lines

PBMCs were isolated as described (Ponath et al., J. Clin. Invest., 97:604–612 (1996)). To generate CD3 blasts, $2 \times 10^6$ PBMC/ml in RPMI-1640 plus 10% FCS were added to tissue culture plates first coated with the anti-CD3 antibody TR77. After 4–6 days, blasts were removed to fresh media and supplemented with recombinant human interleukin 2 (rhIL-2, Hoffmann-LaRoche, Nutley, N.J.) at 100 u/ml. Other cell lines used included THP-1 and transfectants of the L1.2 murine pre B cell lymphoma, expressing high levels of CCR5 (Wu et al., J. Exp. Med., 185:–681–1691 (1997); Wu et al., Nature, 384:179–183 (1996)). Transfectants were maintained in RPMI-1640 supplemented with 10% bovine serum and 800 μg/ml G418 or mycophenolic acid. The different transfectants were monitored for expression of the relevant receptors, using specific mAbs (Qin et al., Eur. J. Immunol., 26:640–647 (1996); Wu et al., J. Exp. Med., 185:1681–1691 (1997)).

Chemokine and HIV-1 gp120 Binding $^{125}$I-labeled human RANTES, $^{125}$I-MIP-1α and $^{125}$I-MIP-1β were purchased from DuPont NEN (Boston, Mass.), and unlabeled chemokines were from Peprotech (Rocky Hill, N.J.). Chemokine binding to target cells was carried out using a modified method previously reported (Wu et al., Nature, 384:179–183 (1996); Van Riper et al., J. Exp. Med., 177:851–856 (1993)). CCR5 L1.2 cells or CD3 blasts were washed and resuspended in binding buffer (50 mM HEPES, pH 7.5, 1 mM $CaCl_2$, 5 mM $MgCl_2$, and 0.5% BSA) at $5 \times 10^6$ cells/ml. For each binding reaction (in a final volume of 100 μl), 25 μl cell suspension ($1.25 \times 10^5$ cells) was mixed with 0.1 nM radiolabeled chemokine, with or without an appropriate amount of anti-CCR5 mAb, or isotype matched control mAb. Total binding was determined in the presence of radio-labeled chemokines only, and non-specific binding (background) was determined in the presence of 100 nM unlabeled chemokines. The reactions were incubated at room temperature for 30–45 minutes, and stopped by transferring the mixture to GFB filter plates, which were then washed 2–3 times with binding buffer containing 0.5 M NaCl. The plates were dried and MicroScint scintillation fluid was added before counting. Each sample was done in duplicate.

The envelope gp120 protein derived from HIV-1 JR-FL (macrophage-tropic) was iodinated using solid phase lactoperoxidase (Bio-Rad) to a specific activity of 20 µCi/µg. CCR5 L1.2 cells were incubated with 0.2 nM $^{125}$I-labeled-gp120 in the absence or presence of increasing concentrations of mAb 2D7 or 3A9. mAb 3A9, produced by the 3A9 hybridoma cell line, is another anti-CCR5 antibody which was produced as described (Example 1). Binding to target cells was performed similarly as for radiolabeled chemokine binding, except that soluble CD4 was included in the assays, as previously reported (Wu et al., *Nature*, 384:179–183 (1996)). An IgG1 control mAb was used as a control.

mAbs, Immunofluorescent Staining, and FACS®Analysis mAb 2D7 reactive with CCR5 was generated by immunizing mice with L1.2 cells expressing high levels of transfected CCR5-Flag, as described (Wu et al., *J. Exp. Med.*, 185:1681–1691 (1997)). C57BL6 mice were immunized with $10^7$ cells, intraperitoneally, six times at 2 week intervals, and four days following an intravenous injection, the spleen was removed and cells were fused with the SP2/0 cell line. The mAb generated, 2D7, was determined to be IgG1. The 2D7 hybridoma cell line (also referred to as LS100-2D7-13-1-1-14-14-4) was deposited on Jun. 6, 1997, on behalf of LeukoSite, Inc., under the terms of the Budapest Treaty at the American Type Culture Collection, 10801 University Boulevard, Manassas, Va. 20110-2209 under Accession Number HB-12366. Other mAbs used in this study included 5A11, an anti-CCR2b mAb (Qin et al., *Eur. J. Immunol.*, 26:640–647 (1996)), and 3A9, an anti-CCR5 mAb (Example 1) that blocks macrophage-tropic HIV-1 infection of human T cells (Wu et al., *J. Exp. Med.*, 185:1681–1691 (1997)).

To assess reactivity of mAbs against transfected cells (including cells transfected with chimeras as described herein) or leukocytes, indirect immunofluorescence and flow cytometry were used. Cells were washed once with PBS, and resuspended in 100 µl PBS containing 2% human serum and 0.1% sodium azide (staining buffer), and 5 µg/ml purified antibody, 5 µg/ml IgG1 or IgG$_{2a}$ isotype-matched control mAb (Sigma Chemical Co., St. Louis, Mo.), or 50 µl hybridoma culture supernatant. After 20 minutes at 4° C., cells were washed twice with staining buffer, and resuspended in 50 µl FITC-conjugated affinity purified F(ab')$_2$ goat anti-mouse IgG (Jackson ImmunoResearch Laboratories). After incubating for 20 minutes at 4° C., cells were washed twice in staining buffer and analyzed on the FACScan® to determine the level of surface expression. Propidium iodide was used to exclude dead cells.

Chemotaxis Assays

Recombinant human chemokines were obtained either from Peprotech (Rocky Hill, N.J.) or R and D systems (Minneapolis, Minn.). Chemotaxis assays with human PBMC or CD3-activated IL-2 stimulated T cells, employed the cell line ECV304 (an endothelial cell line, European Collection of Animal Cell Cultures, Porton Down, Salisbury, U.K.) to coat Biocoat® Transwell tissue culture inserts (Costar Corp., Cambridge, Mass.), and were performed as described (Ponath et al., *J. Clin. Invest.*, 97:604–612 (1996)). Cells migrating to the bottom chamber of the Transwell tissue culture inserts were enumerated using the FACScan®, by counting cells for 30 seconds. Chemotaxis assays with L1.2 receptor transfectant cell lines were as described (Ponath et al., *J. Clin. Invest.*, 97:604–612 (1996)), except that endothelial cells were not used to coat the Biocoat® Transwell tissue culture inserts and the incubation was for 4–6 hours. Tight forward angle and side scatter gates were set on the FACScan® to exclude debris or irrelevant cells.

Measurement of $[Ca^{2+}]_i$

Cells were labeled with the fluorochrome Fura-2 AM (Molecular Probes, Eugene Oreg.), as previously described (Heath et al., *J. Clin. Invest.*, 99:178–184 (1997)). Briefly, Fura-2 AM was added to the cell suspension to produce a final concentration of 0.2 moles/$10^6$ cells. After incubation at 37° C. for 30 minutes, excess dye was removed by centrifugation and cells were resuspended at a concentration of $10^6$ cells/ml in 125 mM NaCl, 5 mM KCl, 1 mM MgCl$_2$, 1 mM CaCl$_2$, 0.5 mM glucose, 0.025% BSA and 20 mM HEPES, pH 7.4. CCR5 L1.2 cells were stimulated sequentially with mAb, followed 40 seconds later with MIP-1α, and 100 seconds following that with SDF-1. $[Ca^{2+}]_i$ fluorescence changes were recorded using excitation at 340 and 380 nm on a Hitachi F-2000 fluorescence spectrometer. Calibration was performed using 1% NP-40 for total release and 25 µM EGTA to chelate free $Ca^{2+/}$·

Inhibition of HIV-1 Infection by Anti-CCR5 mAbs

Inhibition of HIV-1 infection in U87-CD4-CCR5 cells was determined using a virus entry assay based on single-cycle infection. Cells were infected with the env-deficient virus NL4/3 luc (Connor et al., *Virol.* 206:935 (1995)) complemented in trans with envelope glycoproteins from several clones. Infection of the cells was measured by quantification of luciferase activity. Briefly, U87-CD4-CCR5 cells (a gift from D. Littman, New York University Medical Center) were split to a concentration of $5 \times 10^4$ cells/ml, and 100 µl was added to each well of a 96-well tissue culture plate. The following day, the cells were washed with PBS and pre-incubated with dilutions of mAb 2D7, an isotype-control (IgG1) mAb, or medium only in a total volume of 40 µl for 1 hour at 4° C. Fifty microliters of HIV-1 (env genes of ADA, JR-FL, DH123 or HxB2, stocks of 100 ng/ml, as measured by p24) was added, and the cells were incubated with the mAb and the virus for 2 hours at 37° C. The cells were then washed and fresh medium was added, and again after 48 hours. Seventy-two hours post-infection, the cells were washed with PBS and lysed in 50 µl of 1× reporter lysis buffer (Promega). To measure luciferase activity, 100 µl of luciferase substrate (Promega) was added to 30 µl of the cell lysate.

Studies showing inhibition of HIV-1 infection of PBMC by mAb 5C7 were also carried out. Complementation of a single round of replication of the env-deficient chloramphenicol acetyltransferase (CAT)-expressing provirus by various envelope glycoproteins was performed as described in Helseth et al. (*J. Virol.* 64:2416–2420 (1990)) and Thali et al. (*J. Virol.* 67:3978–3988 (1993)). To inhibit viral replication, monoclonal antibody was incubated with target PBMC for 90 minutes at 37° C. before the addition of recombinant virus YU2 (M-tropic) or HxBC2 (T-tropic) to the cells. At three days after infection, the target cells were lysed and CAT activity was measured as described in Helseth et al. (*J. Virol.* 64:2416–2420 (1990)). The results of this study are shown in FIG. 12.

Results

Generation of Anti-CCR5 mAbs that Recognize Different Domains of CCR5

Figure 6A:
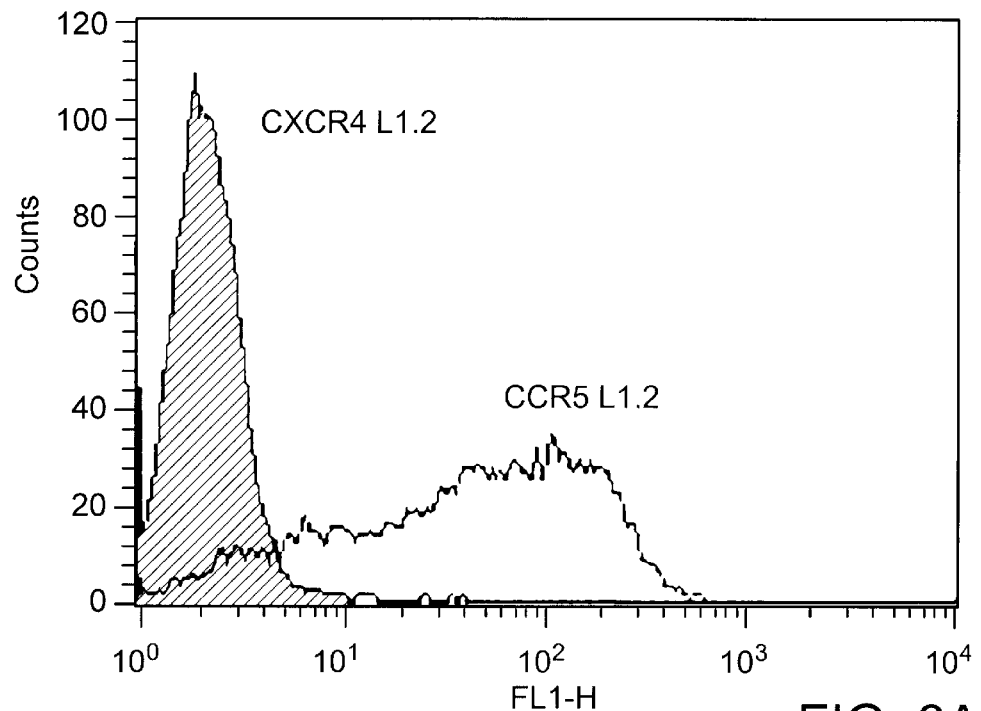
FIGS. 6A and 6B demonstrate that mAb 2D" recognizes the CCR5 receptor.
Figure 6B:
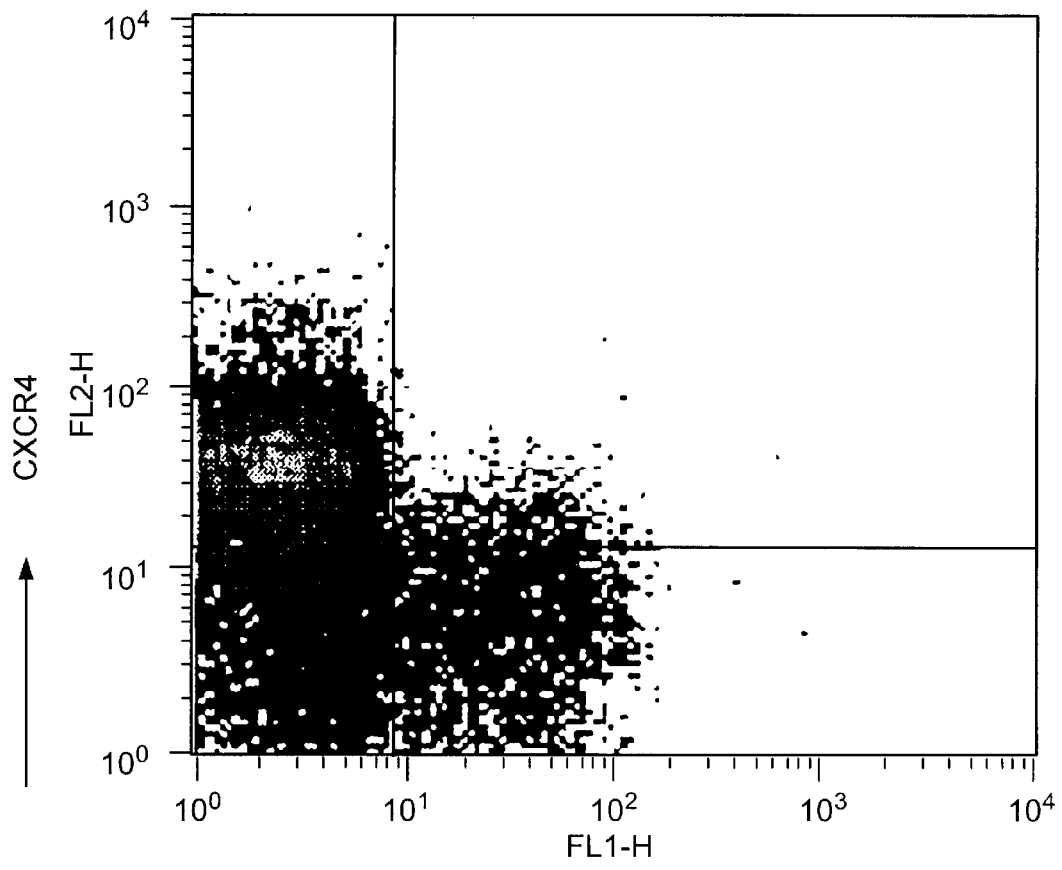

As described herein, mAbs to CCR5 were generated which can inhibit the various functions of this molecule, and can be used to determine how different portions of the molecule bind chemokines or HIV-1. Anti-CCR5 mAbs that inhibit HIV-1 binding, but not ligand binding, have been described (Wu et al., *J. Exp. Med.*, 185:1681–1691 (1997)). Monoclonal antibodies to CCR5 were generated as described herein by immunizing C57BL6 mice with the murine pre-B cell lymphoma line, L1.2, expressing high levels of transfected human CCR5. One mAb generated by this method, termed 2D7, reacted with CCR5-transfected L1.2 cells, as well as CHO cells expressing certain portions of CCR5, but not with L1.2 cells expressing CXCR4 (FIG. 6A) or various other receptors, including CCR2b. Moreover, 2D7 showed a pattern of reactivity against human leukocytes which appeared to be identical to that previously noted for other anti-CCR5 mAbs (Wu et al., *J. Exp. Med.*, 185:1681–1691 (1997); Bleul et al., *Proc. Natl. Acad. Sci., USA*, 94:1925–1930 (1997)). In particular, 2D7 stained mostly the CXCR4- subset of human peripheral blood lymphocytes (PBL) (FIG. 6B), as well as a subset of tissue macrophages.

Figures 8A, 8B:
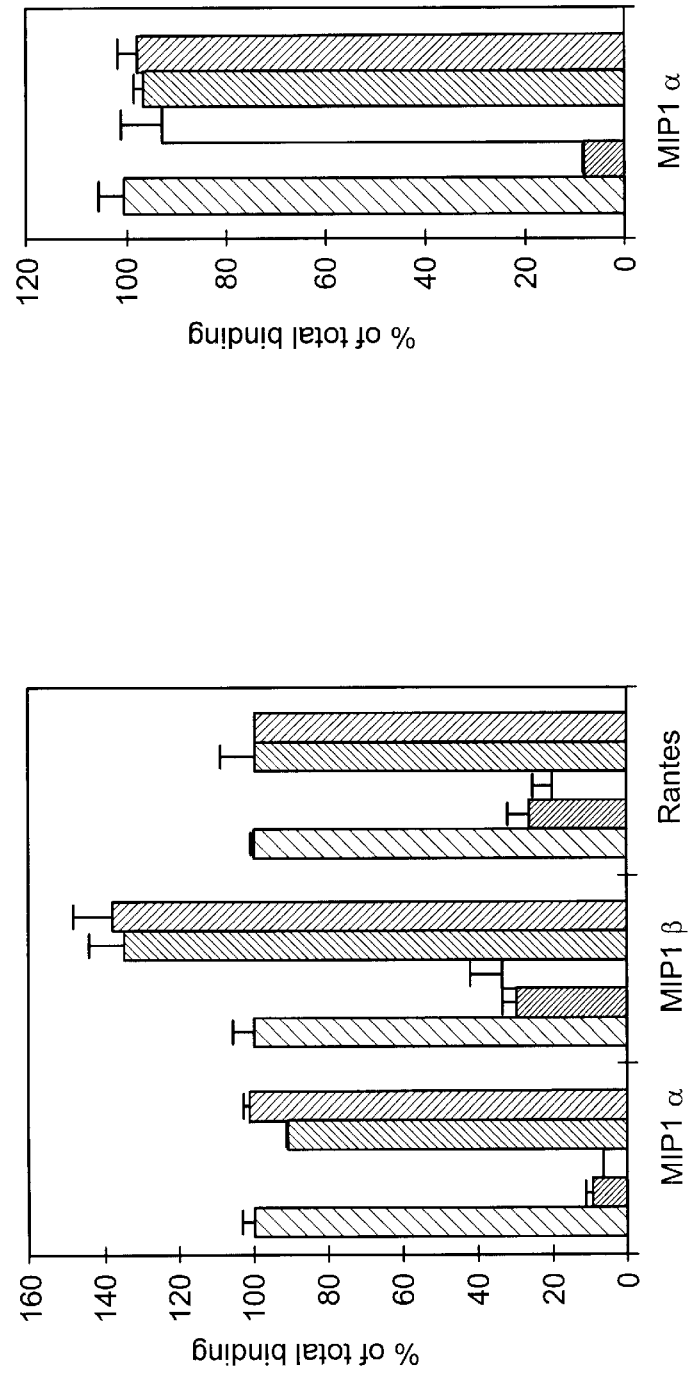
FIGS. 8A–8C are histograms illustrating that mAb 2D7 inhibits ligand binding to CCR5. CCR5 L1.2 cells (FIG. 8A), THP1 cells (FIG. 8B), or CD3 blasts (FIG. 8C) were incubated with 0.1 nM $^{125}$I-labeled-MIP-1α, $^{125}$I-labeled-MIP-1β, or $^{125}$I-labeled-RANTES, in the absence (total binding; stippled bar) or presence of either 10 μg/ml of mAb 2D7 (an IgG1 isotype; unshaded bar), mAb 3A9 (right horizontal-striped bar), control IgG1 mAb (left horizontal-striped bar), or 100 nM unlabeled chemokine (gray shaded bar). Data are shown as the % of total binding which is in the absence of mAb or unlabeled chemokines.

To determine how chemokines or HIV-1 interact with CCR5, a series of chimeric receptors were generated by replacing extracellular domains of human CCR5 with the corresponding domain of human CCR2b, or vice versa, using common restriction sites in regions conserved between the two molecules (Rucker et al., *Cell*, 87:437–446 (1996)). The chimeras of CCR5 and CCR2b were ideal for this purpose, since these two receptors are closely related, but have different ligand binding properties. The interaction of these chimeras with different strains of HIV-1 has already been reported (Rucker et al., *Cell*, 87:437–446 (1996)). FIG. 7 shows the panel of chimeras that was used in the present experiments, and the reactivity of these chimeras to several mAbs. The 2D7 mAb reacted with all chimeras that contained the second extracellular loop of CCR5. In particular, C25-14, a receptor chimera comprising CCR2b with the second extracellular loop of CCR5, was stained intensely by mAb 2D7. In contrast, the anti-CCR5 mAb 3A9 and seven other anti-CCR5 mAbs (5C7, 2F9, 3D8, 2C4, 5D7, 5H11, and 1G4; see Example 1 and Wu et al., *J. Exp. Med.*, 185:1681–1691 (1997)) reacted only with chimeras that contained the amino-terminal region of CCR5 (FIG. 7). In addition, mutants of CCR5 lacking the amino-terminal 8 amino acids were unstained by mAb 3A9, suggesting that the epitope for this mAb was dependent on the amino-terminus of the molecule. A mAb to CCR2b, designated 5A11, stained all chimeras containing the amino-terminus of CCR2b, consistent with the fact that this mAb was raised against a synthetic peptide comprising the 32 amino terminal amino acids of CCR2b (Qin et al., *Eur. J. Immunol.*, 26:640–647 (1996)).

mAb 2D7, Having Specificity for the Second Extracellular Loop of CCR5, Blocks MIP-1α, MIP-1β and RANTES Binding to CCR5 Transfectants and to Activated T Cells A preliminary analysis of a panel of anti-CCR5 mAbs revealed that none of eight anti-CCR5 mAbs (3A9, 5C7, 2F9, 3D8, 2C4, 5D7, 5H11, or 1G4; see Example 1 and Wu et al., *J. Exp. Med.*, 185:1681–1691 (1997)) was able to block the binding of CCR5 ligands RANTES, MIP-1α or MIP-1β to CCR5 L1.2 transfectants under the conditions used. The ability of the new rmAb to inhibit the binding of these ligands was assessed. FIG. 8A shows that 10 μg/ml of mAb 2D7 was able to inhibit completely the binding of $^{125}$I-labeled human RANTES, $^{125}$I-MIP-1α and $^{125}$I-MIP-1β to these transfectants. An analysis with decreasing amounts of mAb 2D7 established an IC$_{50}$ of 23 ng/ml for MIP-1α binding, 41 ng/ml for MIP-1β binding, and 58 ng/ml for RANTES binding. mAb 3A9, directed to the amino-terminus of CCR5, showed little inhibition of binding of the three ligands at 10 μg/ml (FIG. 8A), and only slight inhibition at a concentration up to 100 μg/ml. THP-1 cells, which do not express CCR5 (Wu et al., *J. Exp. Med.*, 185:1681–1691 (1997)), were also examined. These cells bound $^{125}$I-MIP-1α (FIG. 8B) and $^{125}$I-RANTES, however mAb 2D7 had no effect on the level of binding. The predominant receptor on these cells is presumably CCR1.

Figure 8C:
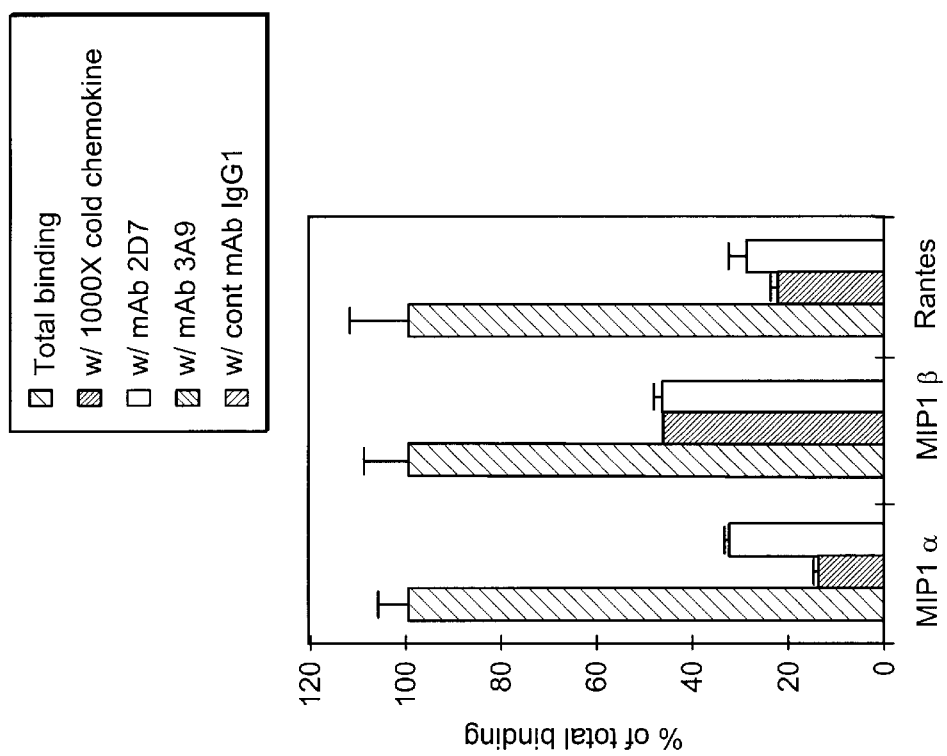

$^{125}$I-RANTES, $^{125}$I-MTP-1α and $^{125}$I-MIP-1β binding to activated T cells is shown in FIG. 8C. These three ligands bound to IL-2 maintained T cells, and such binding could be competed with 100 nM unlabeled chemokine. Day 21 post activation T cells showed the highest level of binding and chemotactic responses to the three ligands (see below). mab 2D7 was assessed for its ability to compete for binding of these three ligands. At 10 μg/ml, 2D7 completely blocked $^{125}$I-MIP-1β binding to these activated T cells. Under the same conditions, the $^{125}$I-RANTES and $^{125}$I-MIP-1α binding were inhibited by 95% and 85%, respectively. This result indicated that CCR5 was responsible for most of the RANTES, MIP-1α or MIP-1β binding to these T cells. However, some variations were noted in the 2D7 inhibition level when using T cells from different time points (10–26 days). At earlier time points, fewer RANTES and MIP-1α binding sites were blocked by mAb 2D7. These data suggest that CCR5 and other receptors are differentially regulated.

mAb 2D7 Inhibits MIP-1α, MIP-1β and RANTES Functional Responses

Chemokines are capable of selectively inducing chemotaxis of the formed elements of the blood (other than red blood cells), including leukocytes such as neutrophils, monocytes, macrophages, eosinophils, basophils, mast cells, and lymphocytes, such as T cells and B cells. In addition to stimulating chemotaxis, other changes can be selectively induced by chemokines in responsive cells, including changes in cell shape, transient rises in the concentration of intracellular free calcium ions ($[Ca^{2+}]_i$), granule exocytosis, integrin upregulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

Figure 9A:
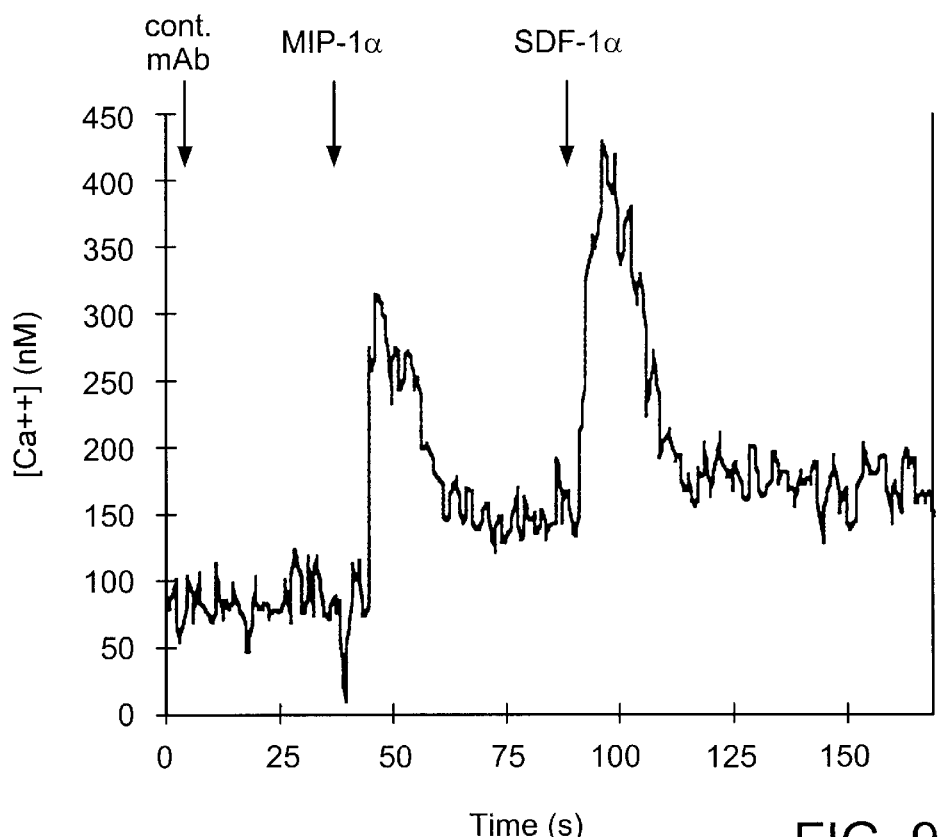
FIGS. 9A and 9B are tracings illustrating that mAb 2D7 inhibits transient increases in the concentration of intracellular free calcium ions ([$Ca^{2-}$]$_i$) in CCR5 L1.2 cells induced in response to MIP-1α, but not in response to SDF-1α. The tracings are representative of three separate experiments.
Figure 9B:
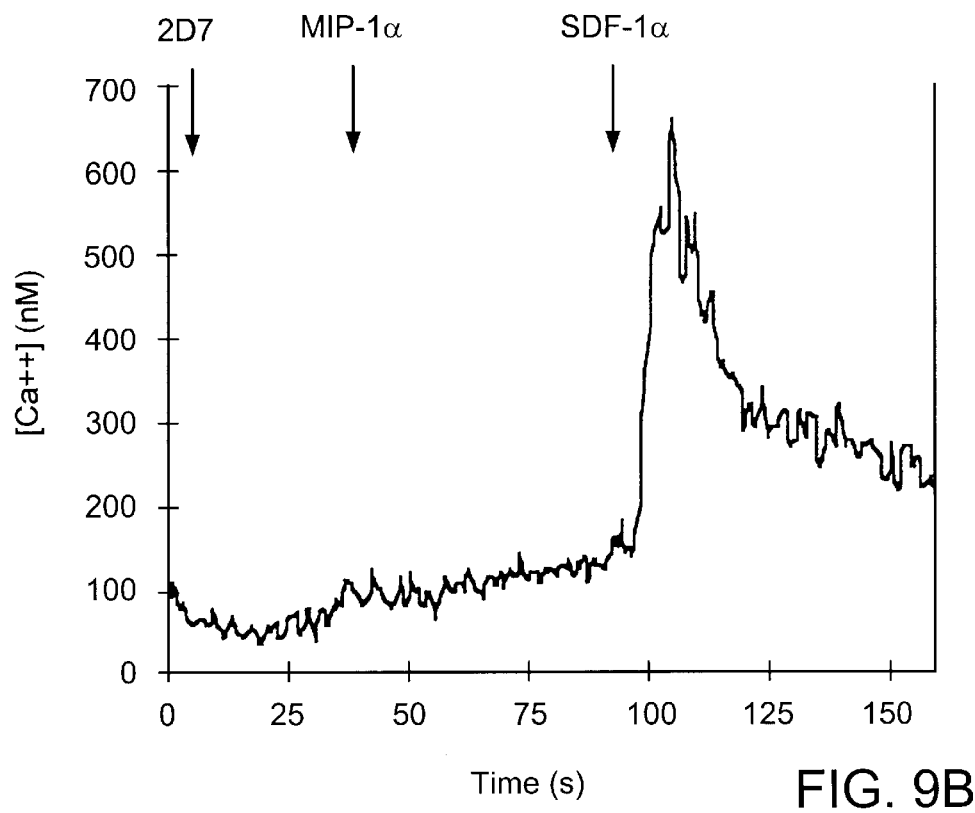
Figure 10A:
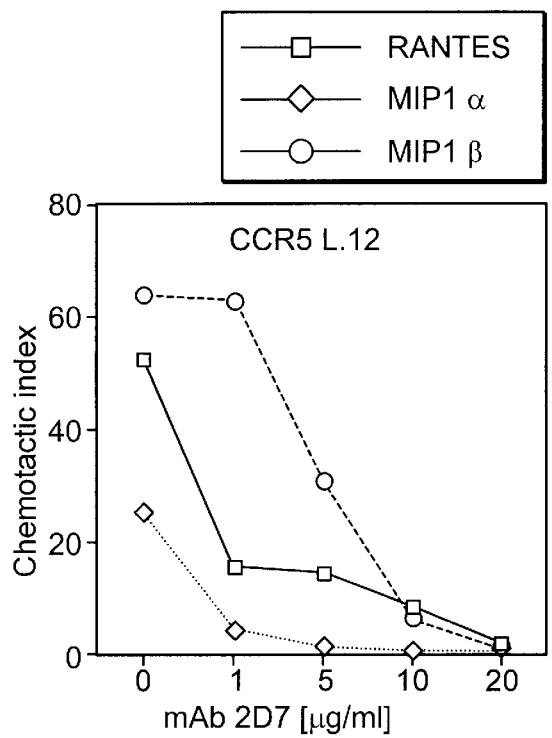
FIGS. 10A–10D are graphs illustrating the inhibition of chemotactic responses of various cell types to MIP-1α, MIP-1β, or RANTES, using mAb 2D7.
Figure 10B:
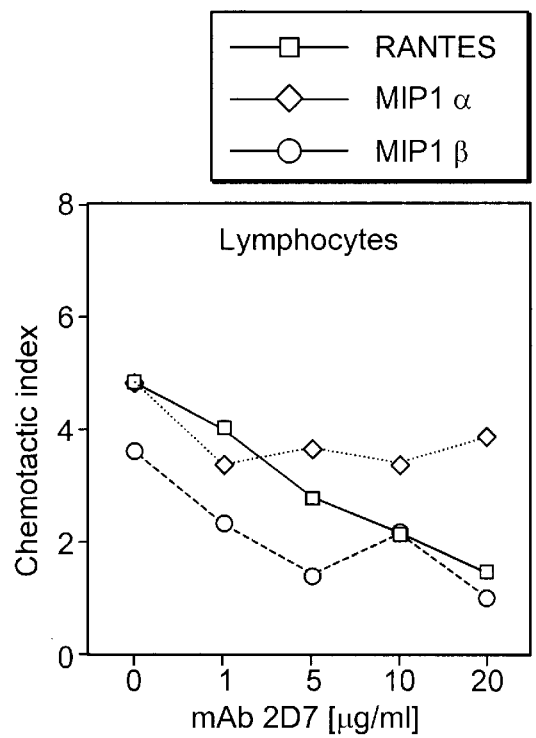

The agonist/antagonist activity of mAb 2D7 was tested on CCR5 L1.2 transfectants, by measuring the change in intracellular calcium concentration $[Ca^{2+}]_i$ of Fura-2 loaded cells stimulated with various concentrations of mAb 2D7 (FIG. 9B). mAb 2D7 did not itself stimulate a change in $[Ca^{2+}]_i$ in CCR5 L1.2 cells, but was able to inhibit subsequent stimulation by MIP-1α (FIG. 9B), as well as by RANTES and MIP-1β. mAb 2D7 did not inhibit a change in $[Ca^{2+}]_i$ following stimulation with SDF-1, which operates through an endogenous mouse CXCR4 receptor. Incubation of CCR5 L1.2 cells with a control mAb (MOPC-21) had no inhibitory effect. Neither mAb 3A9 nor any of the other mAbs having binding specificity for the amino-terminal region of CCR5 had any inhibitory effect on the RANTES, MIP-1α or MIP-1β responses.

mAb 2D7 inhibited the chemotaxis of CCR5 L1.2 cells in response to RANTES, MIP-1α and MIP-1β, in a dose-dependent manner (FIG. 10A). Incubation of cells with 20 μg/ml of mAb in the top chamber was sufficient to achieve complete inhibition of migration to all of the ligands. This fully antagonistic mAb to CCR5, able to block responses through this receptor, allowed us to examine the significance of this receptor for lymphocyte (FIG. 10B), monocyte (FIG.

Figure 10C:
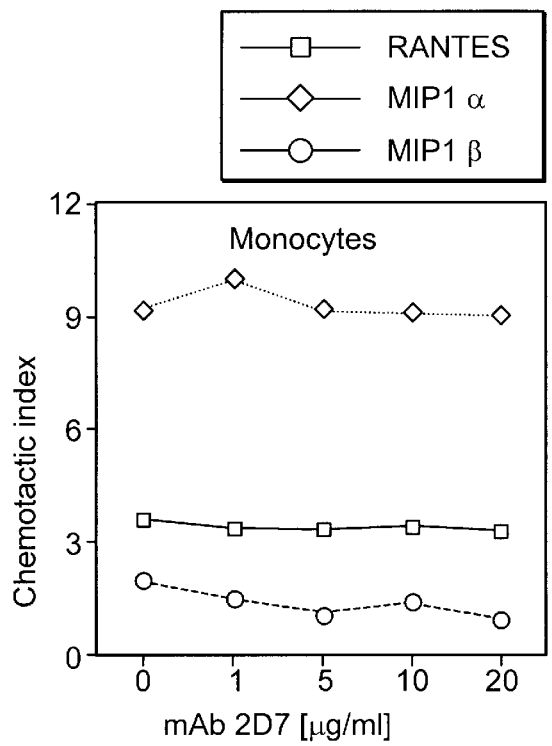
Figure 10D:
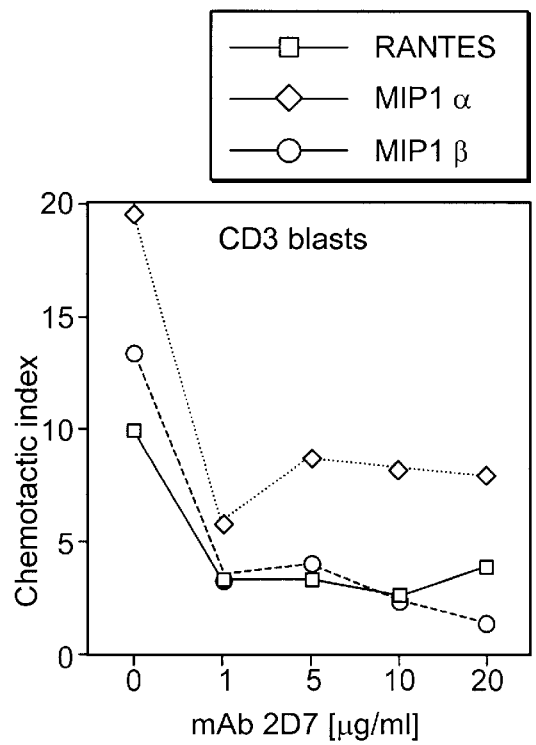

10C) and activated T cell responses (FIG. 10D) to RANTES, MIP-1α and MIP-1β. Chemotactic responses by blood lymphocytes to MIP-1β were totally inhibited by 2D7 (FIG. 10B), consistent with the notion that MIP-1β binds only CCR5 and not other receptors. RANTES responses were also inhibited in most individuals, however MIP-1α responses were not. mAb 2D7 did not inhibit chemotaxis of monocytes to RANTES or MIP-1α (FIG. 10C), presumably because these responses were occurring through CCR1. This result agrees with previous studies showing minimal expression of CCR5 on most monocytes (Wu et al., *J. Exp. Med.,* 185:1681–1691 (1997)). T cells stimulated in vitro with anti-CD3 and maintained with IL-2 for 3 weeks showed a very robust chemotactic response to RANTES, MIP-1α and MIP-1β (FIG. 10D). T cells maintained in culture for shorter periods of time also responded but not quite as robustly (not shown). Importantly, mAb 2D7 was able to inhibit most of the functional chemotactic responses of these T cells to RANTES and MIP-1β, and about 60–80% of the chemotactic response to MIP-1α. However, individual to individual variation was observed. These results were supported by studies with T cell lines from Δ32 homozygous individuals. The MIP-1α and RANTES chemotactic responses were markedly impaired in these T cell lines.

In general, these results are consistent with CCR5 being an important RANTES, MIP-1β and MIP-1α receptor on activated/effector T cells, but having little role in the chemotactic responses of blood monocytes.

Figure 11A:
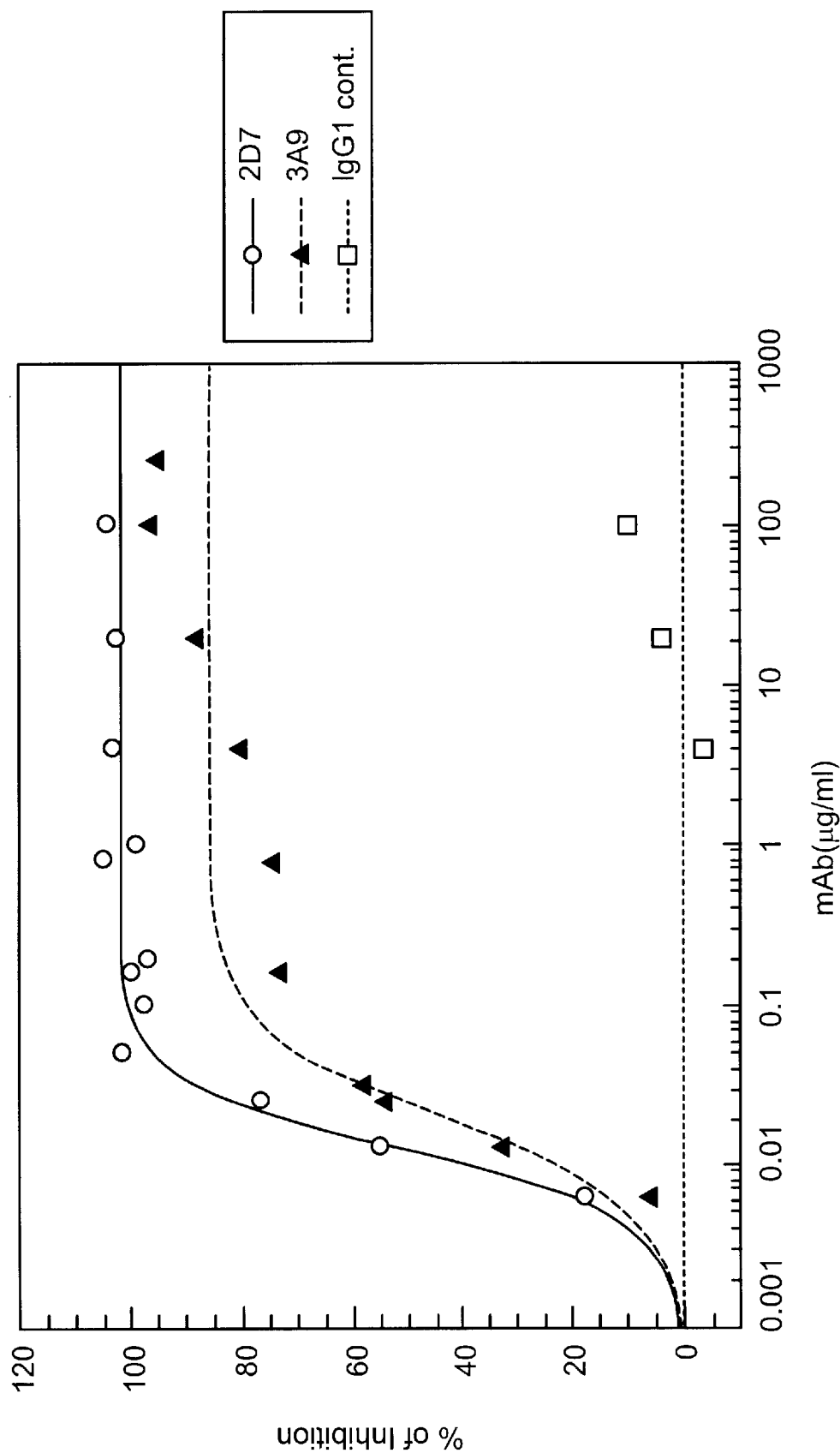
FIGS. 11A and 11B illustrate the inhibition of radiolabeled gp120 binding and HIV-1 infection by anti-CCR5 mAbs.

Inhibition of gp120 Binding to CCR5 is Manifested by mAbs Recognizing Either the Amino-terminus or the Second Extracellular Loop It was reported previously that the exterior envelope glycoprotein gp120 of macrophage-tropic primary HIV-1, upon binding to soluble CD4, can interact with CCR5 specifically and with high affinity (Wu et al., *Nature*, 384:179–183 (1996); Trkola et al., *Nature* 384:184–186 (1996)). To assess the ability of the various anti-CCR5 mAbs to inhibit such an interaction, binding assays were performed using $^{125}$I-labeled gp120 derived from HIV-1 JR-FL (a macrophage-tropic strain) in the presence or absence of mAb 3A9 or mAb 2D7 (FIG. 11A). mAb 2D7 inhibited efficiently the binding of $^{125}$I-gp120 to CCR5 L1.2 cells, in the presence of soluble CD4, with an $IC_{50}$ of approximately 10 ng/ml. At a concentration of 50 ng/ml, 2D7 inhibited the binding of radiolabeled gp120 completely, to the same level as that obtained with excess unlabeled gp120. In contrast, mAb 3A9 had a moderate inhibitory effect on the $^{125}$I-gp120 binding at a lower concentration range, but it inhibited completely when a higher concentration (greater than approximately 100 μg/ml) of mAb was used, which is consistent with the previous finding that 3A9 can neutralize the infection of PBMC by macrophage-tropic HIV-1 strains (Wu et al., *J. Exp. Med.,* 185:1681–1691 (1997)). As expected, an isotype-control mAb did not have any significant inhibitory effect at a concentration up to 100 μg/ml.

Thus, efficient inhibition of a M-tropic HIV-1-derived gp120 binding to CCR5 could be achieved with mAbs recognizing either the second extracellular loop, or the amino-terminal region, although the former showed superior inhibition. These results suggest that agonists or antagonists that bind the second extracellular loop of CCR5 can serve as potent inhibitors of gp120 binding to CCR5, even though this loop can be redundant for HIV-1 gp120 binding.

Monoclonal antibody 2D7, prepared as described herein, was able to totally inhibit the binding of RANTES, MIP-1α, and MIP-1β, while mAbs recognizing the N-terminus of CCR5 did not display similar activity under the conditions used. mAb 2D7 was able to completely inhibit the binding of gp120 of HIV-1 JR-FL (a macrophage-tropic strain) to CCR5, despite the fact that the amino-terminus of CCR5 also contributes to gp120 interactions. Studies with CCR5/CCR2b chimeras showed that JR-FL gp120 binding appears to rely more on the amino-terminus and the first extracellular loop (Rucker et al., *Cell,* 87:437–446 (1996)). The ability of an agent to inhibit HIV-1 binding may have more to do with steric hinderance rather than direct interruption of the important binding site.

Figure 11B:
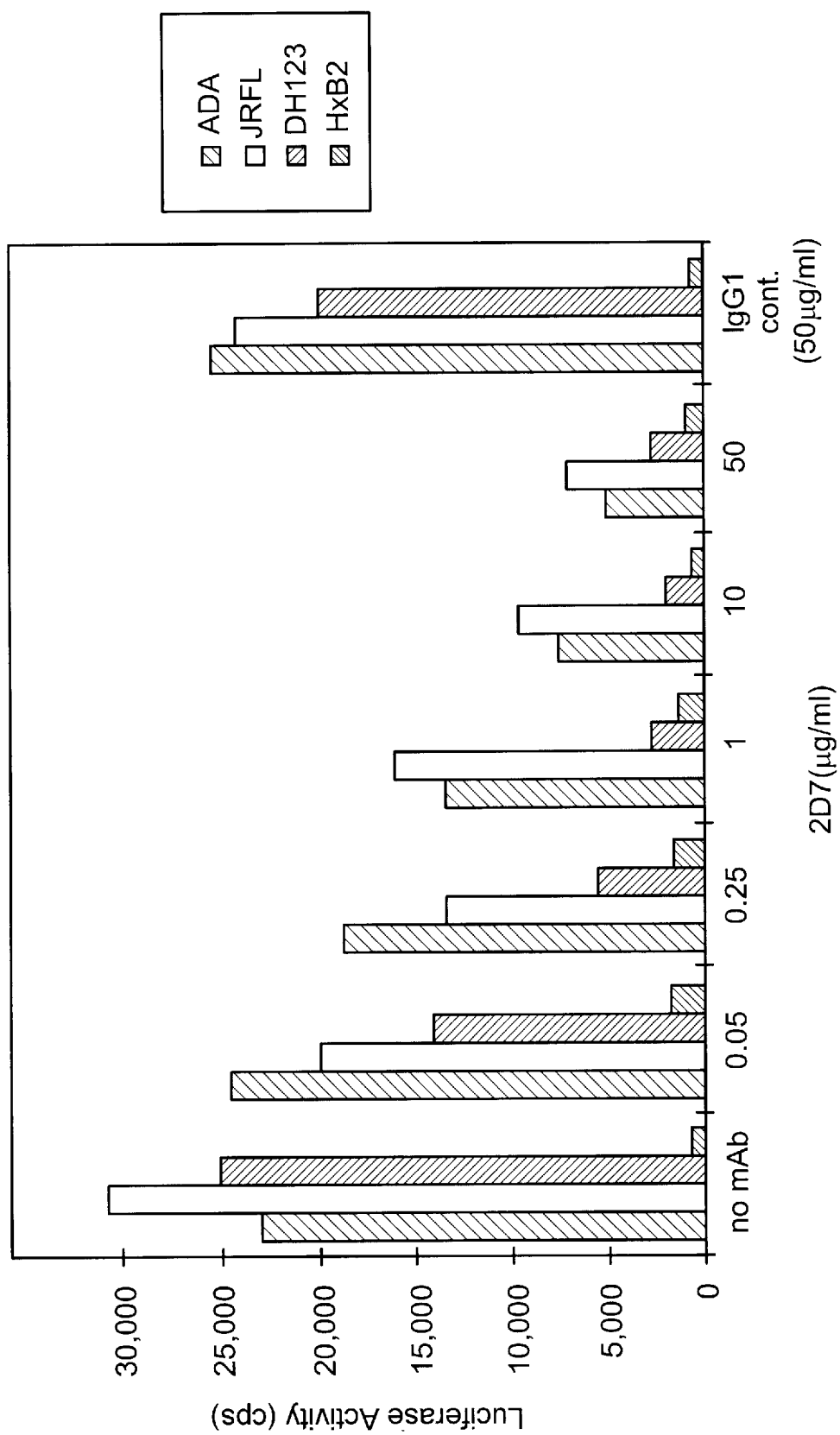
Figure 12A:
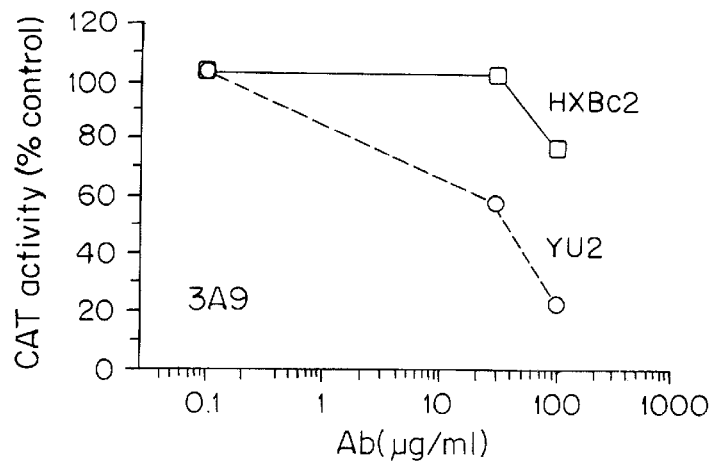
FIGS. 12A–12F are graphs showing inhibition of HIV-1 infection of PBMC by various anti-CCR5 mAbs.
Figure 12B:
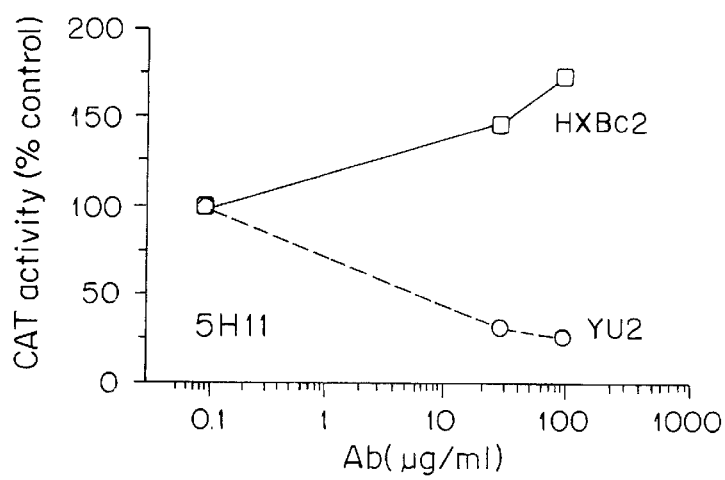
Figure 12C:
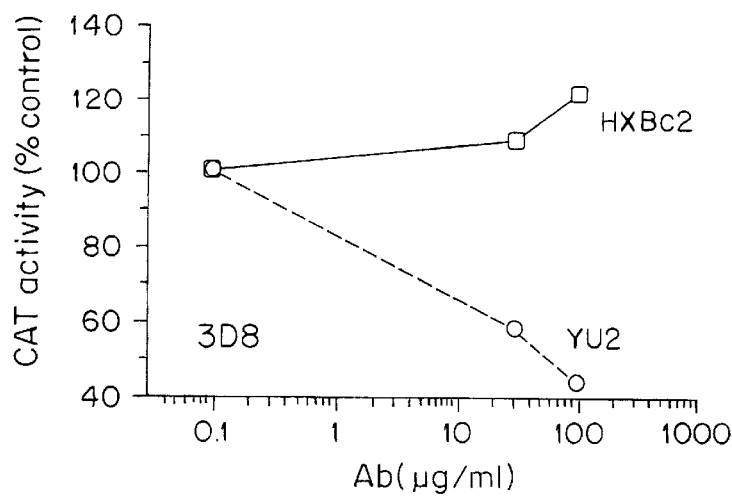
Figure 12D:
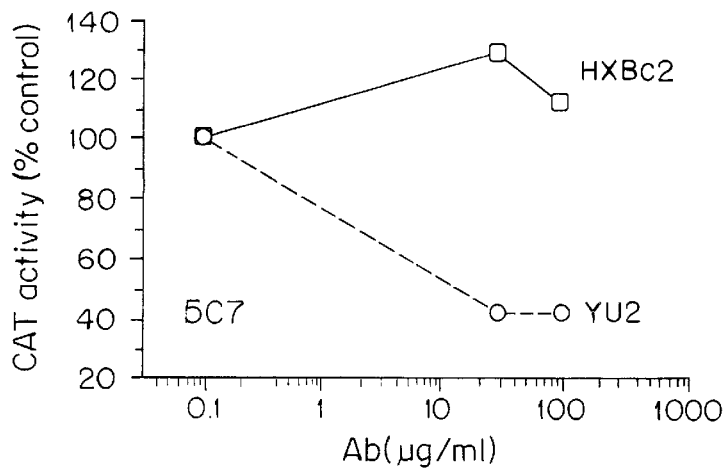
Figure 12E:
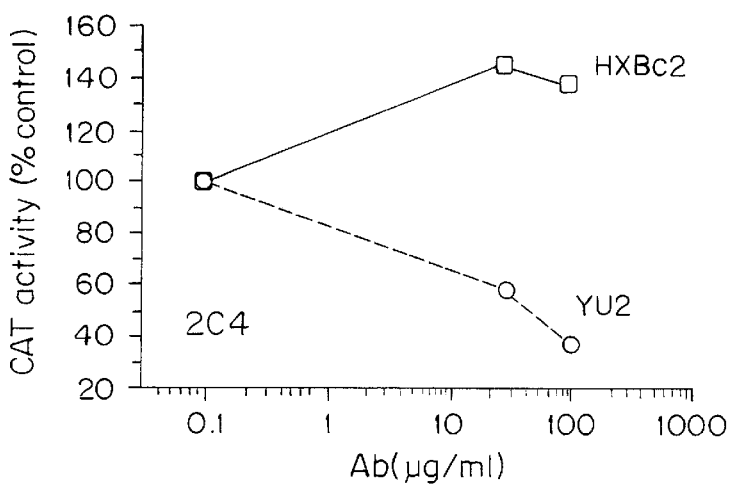
Figure 12F:
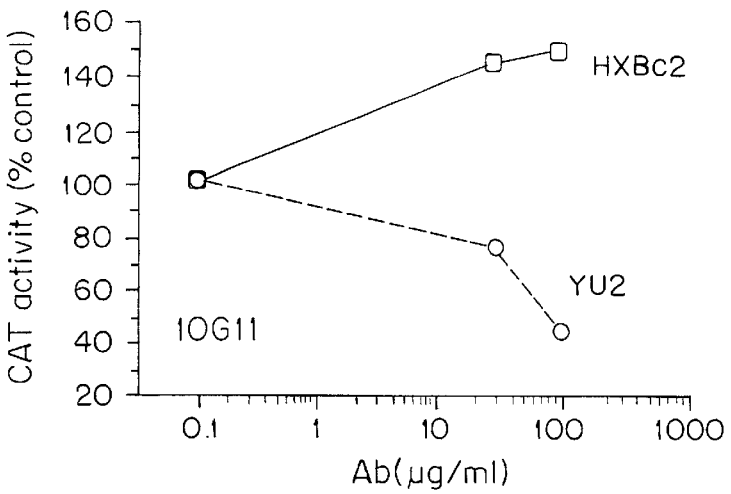

In order to assess the inhibitory effect of 2D7 on HIV-1 entry, a virus entry assay based on single-cycle infection using several viral strains was employed. As shown in FIG. 11B, the U87MG-CD4+ cells expressing CCR5 can be efficiently infected by M-tropic (ADA and JR-FL env) and dual-tropic (DH123 env) chimeric viruses, which can use CCR5 as a co-receptor, but not by the T cell-tropic chimera HxB2), which uses only CXCR4. mAb 2D7 efficiently inhibited the entry of the dual-tropic DH123 chimera (>90% inhIbition at 1 μg/ml), whereas a higher concentration of 2D7 (approximately 10 μg/ml for approximately 90% inhibition) was required for inhibiting the M-tropic (ADA and JR-FL). Under the same conditions, the inhibitory effect of mAb 3A9 and 5C7 were weaker, and the isotype-control mAb had no significant effect.

Anti-CCR5 mAbs whose binding specificity mapped to the amino-terminus were also able to inhibit HIV-1 entry into T cells. This result is consistent with a contribution of the amino-terminus for HIV-1 binding (Rucker et al., *Cell,* 87:437–446 (1996)), and the fact that HIV-1 entry and response to chemokines are somewhat non-overlapping functions of CCR5 (Atchison et al., *Science,* 274: 1924–1926 (1996); Farzan et al., *J. Biol Chem* 272(11) :6854–6857 (1997). Therefore, whereas specificity of ligand binding to CCR5 is determined by a single domain, the binding of gp120 is more complex and involves at least two domains. As shown herein, total inhibition of gp120 binding to CCR5 can be achieved with mAbs directed against either the amino terminus, or the second extracellular loop, particularly for gp120 from macrophage-tropic isolates. It appears that mAb 2D7 will block CCR5 binding to gp120 of most HIV-1 strains, particularly those which can use CCR5 as a co-receptor, since mAb 2D7 is able to block entry of a wide range of macrophage-tropic and dual tropic isolates (FIG. 11B). The potential to disrupt HIV-1 gp120 binding with agents that interfere with either the amino-terminus or the second extracellular loop suggest that similarly acting small molecule antagonists, binding to one or more of these or other regions of CCR5, can also be effective at blocking CCR5-gp120 interactions. Antibodies of the present invention can be used in competition binding studies to identify agents which can compete for binding to one or more of these regions, and which are potential inhibitors (e.g., antagonists) or promoters (e.g., agonists) of mammalian CCR5 function.

The mAb 2D7 blocked RANTES, MIP-1α and MIP-1β chemotactic responses by T cell lines from most individuals. In most cases, only partial (60–80%) inhibition of RANTES and MIP-1α responses was observed, suggesting that although CCR5 is the predominant RANTES and MIP-1α receptor, and the only MIP-1β receptor on T cells, other receptors play a role for RANTES and MIP-1α responses.

Equivalents

Those skilled in the art will be able to recognize, or be able to ascertain, using no more than routine experimentation, many equivalents to the specific embodiments of the invention described herein. Such equivalents are intended to be encompassed by the following claims.

We claim:

1. An antibody or antigen binding fragment thereof which binds to a mammalian chemokine receptor 5 (CCR5), wherein said antibody has the epitopic specificity of a monoclonal antibody produced by the hybridoma deposited under ATCC Accession No. HB-12366.

2. The antibody or antigen binding fragment thereof of claim 1, wherein the mammalian chemokine receptor 5 (CCR5) is a human chemokine receptor 5 (CCR5).

3. The antibody or antigen binding fragment thereof of claim 1, wherein said antibody or antigen binding fragment thereof inhibits binding of one or more chemokines selected from the group consisting of MIP-1α, MIP-1β and RANTES to the receptor.

4. The antibody or antigen binding fragment thereof of claim 3, wherein said antibody or antigen binding fragment thereof inhibits one or more functions associated with binding of said one or more chemokines to the receptor.

5. The antibody or antigen binding fragment thereof of claim 1, wherein the antibody is a monoclonal antibody produced by the hybridoma deposited under ATCC Accession No. HB-12366 or wherein the antigen binding fragment is an antigen binding fragment of a monoclonal antibody produced by the hybridoma deposited under ATCC Accession No. HB-12366.

6. The antibody or antigen binding fragment thereof of claim 1, wherein the antibody or antigen binding fragment is a monoclonal antibody or antigen binding fragment thereof.

7. The antibody or antigen binding fragment thereof of claim 1, wherein the antibody or antigen binding fragment is a chimeric antibody or antigen binding fragment thereof.

8. The antibody or antigen binding fragment thereof of claim 1, wherein the antibody or antigen binding fragment is a human antibody or antigen binding fragment thereof.

9. The antibody or antigen binding fragment thereof of claim 1, wherein the antibody or antigen binding fragment is a humanized antibody or antigen binding fragment thereof.

10. The antibody or antigen binding fragment thereof of claim 9, wherein the humanized antibody comprises the six complementarity determining regions of a monoclonal antibody produced by the hybridoma deposited under ATCC Accession No. HB-12366 and a portion of an immunoglobulin of human origin.

11. The antibody or antigen binding fragment thereof of claim 1, wherein the antigen binding fragment is selected from the group consisting of an Fv fragment, an Fab fragment, an Fab' fragment and an F(ab')$_2$ fragment.

12. A composition comprising an antibody or antigen binding fragment thereof which binds to a mammalian chemokine receptor 5 (CCR5), wherein said antibody has the epitopic specificity of a monoclonal antibody produced by the hybridoma deposited under ATCC Accession No. HB-12366.

13. The composition of claim 12, wherein the mammalian chemokine receptor 5 (CCR5) is a human chemokine receptor 5 (CCR5).

14. The composition of claim 12, wherein said antibody or antigen binding fragment thereof inhibits binding of one or more chemokines selected from the group consisting of MIP-1α, MIP-1β and RANTES to the receptor.

15. The composition of claim 14, wherein said antibody or antigen binding fragment thereof inhibits one or more functions associated with binding of said one or more chemokines to the receptor.

16. The composition of claim 12, wherein the antibody is a monoclonal antibody produced by the hybridoma deposited under ATCC Accession No. HB-12366 or wherein the antigen binding fragment thereof is an antigen binding fragment of a monoclonal antibody produced by the hybridoma deposited under ATCC Accession No. HB-12366.

17. The composition of claim 12, wherein the antibody or antigen binding fragment is a monoclonal antibody or antigen binding fragment thereof.

18. The composition of claim 12, wherein the antibody or antigen binding fragment is a chimeric antibody or antigen binding fragment thereof.

19. The composition of claim 12, wherein the antibody or antigen binding fragment is a human antibody or antigen binding fragment thereof.

20. The composition of claim 12, wherein the antibody or antigen binding fragment is a humanized antibody or antigen binding fragment thereof.

21. The composition of claim 20, wherein the humanized antibody comprises the six complementarity determining regions of a monoclonal antibody produced by the hybridoma deposited under ATCC Accession No. HB-12366 and a portion of an immunoglobulin of human origin.

22. The composition of claim 12, wherein the antigen binding fragment is selected from the group consisting of an Fv fragment, an Fab fragment, an Fab' fragment and an F(ab')$_2$ fragment.

23. A test kit for use in detecting the presence of a mammalian chemokine receptor 5 (CCR5) in a biological sample comprising:
   a) an antibody or antigen binding fragment thereof which binds to a mammalian chemokine receptor 5 (CCR5), wherein said antibody has the epitopic specificity of a monoclonal antibody produced by the hybridoma deposited under ATCC Accession No. HB-12366; and
   b) one or more ancillary reagents suitable for detecting the presence of a complex between said antibody or antigen binding fragment thereof and said receptor.

24. A bispecific antibody or antigen binding fragment thereof having as one specificity the epitopic specificity of a monoclonal antibody produced by the hybridoma deposited under ATCC Accession No. HB-12366.

25. A bispecific antibody or antigen binding fragment thereof which binds the second extracellular loop of a mammalian chemokine receptor 5 (CCR5) and the amino terminal region of a mammalian chemokine receptor 5 (CCR5).

26. A test kit for use in detecting the presence of a mammalian chemokine receptor 5 (CCR5) in a biological sample comprising:
   a) a bispecific antibody or antigen binding fragment thereof having as one specificity the epitopic specificity of a monoclonal antibody produced by the hybridoma deposited under ATCC Accession No. HB-12366; and
   b) one or more ancillary reagents suitable for detecting the presence of a complex between said antibody or antigen binding fragment thereof and said receptor.

27. A test kit for use in detecting the presence of a mammalian chemokine receptor 5 (CCR5) in a biological sample comprising:
   a) a bispecific antibody or antigen binding fragment thereof which binds the second extracellular loop of a mammalian chemokine receptor 5 (CCR5) and the amino terminal region of a mammalian chemokine receptor 5 (CCR5); and
   b) one or more ancillary reagents suitable for detecting the presence of a complex between said antibody or antigen binding fragment thereof and said receptor.

28. A bispecific antibody or antigen binding fragment thereof having the epitopic specificity of a monoclonal antibody produced by the hybridoma deposited under ATCC Accession No. HB-12366 and a monoclonal antibody produced by the hybridoma deposited under ATCC Accession No. HB-12222.

29. A test kit for use in detecting the presence of a mammalian chemokine receptor 5 (CCR5) in a biological sample comprising:
   a) a bispecific antibody or antigen binding fragment thereof having the epitopic specificity of a monoclonal antibody produced by the hybridoma deposited under ATCC Accession No. HB-12366 and a monoclonal antibody produced by the hybridoma deposited under ATCC Accession No. HB-12222; and
   b) one or more ancillary reagents suitable for detecting the presence of a complex between said antibody or antigen binding fragment thereof and said receptor.

30. The hybridoma cell line deposited under ATCC Accession No. HB-12366.

31. A monoclonal antibody produced by the hybridoma cell line deposited under ATCC Accession No. HB-12366.

32. An antigen binding fragment of a monoclonal antibody produced by the hybridoma cell line deposited under ATCC Accession No. HB-12366.

33. The antigen binding fragment of claim 32, wherein said antigen binding fragment is an Fv fragment.

34. The antigen binding fragment of claim 32, wherein said antigen binding fragment is an Fab fragment.

35. The antigen binding fragment of claim 32, wherein said antigen binding fragment is an Fab' fragment.

36. The antigen binding fragment of claim 32, wherein said antigen binding fragment is an $F(ab')_2$ fragment.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO:1:

ATTTTCCATA CAGTCAGTAT CAATTCTGGA AGAATTTCCA GACATTAAAG ATAGTC           56

(2) INFORMATION FOR SEQ ID NO:2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:2:

ATTTTCCATA CATTAAAGAT AGTC                                              24

(2) INFORMATION FOR SEQ ID NO:3:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO:3:

CCCCTCGAGA TGGACTACAA GGACGACGAT GACAAGGATT ATCAAGTGTC AAGTCC           56

(2) INFORMATION FOR SEQ ID NO:4:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:4:

CCCTCTAGAT TACAAGCCCA CAGATATTTC CTGCTCCCC                              39

(2) INFORMATION FOR SEQ ID NO:5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:5:

GAAGTTCCTC ATTACACCTG CAGCTCTC                                          28

(2) INFORMATION FOR SEQ ID NO:6:

(i) SEQUENCE CHARACTERISTICS:
        (A) LENGTH: 29 base pairs
        (B) TYPE: nucleic acid
        (C) STRANDEDNESS: single

```
          (D) TOPOLOGY: linear (xi) SEQUENCE DESCRIPTION: SEQ ID NO:6:

CTTCTTCTCA TTTCGACACC GAAGCAGAG                                        29

(2) INFORMATION FOR SEQ ID NO:7:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:7:

Asp Tyr Lys Asp Asp Asp Asp Lys
  1               5
```